(12) United States Patent
Roschin et al.

(10) Patent No.: US 11,707,344 B2
(45) Date of Patent: Jul. 25, 2023

(54) SEGMENTATION QUALITY ASSESSMENT

(71) Applicant: Align Technology, Inc., San Jose, CA (US)

(72) Inventors: Roman A. Roschin, Moscow (RU); Evgenii Vladimirovich Karnygin, Moscow (RU); Sergey Grebenkin, Moscow (RU); Dmitry Guskov, Moscow (RU); Dmitrii Ischeykin, Moscow (RU); Ivan Potapenko, Berdsk (RU); Denis Durdin, Novosibirsk (RU); Roman Gudchenko, Moscow (RU); Vasily Paraketsov, Moscow (RU); Mikhail Gorodilov, Novosibirsk (RU); Roman Solovyev, Novosibirsk (RU); Alexey Vladykin, Balashikha (RU); Alexander Beliaev, Moscow (RU); Alexander Vovchenko, Moscow (RU)

(73) Assignee: Align Technology, Inc., San Jose, CA (US)

(*) Notice: Subject to any disclaimer, the term of this patent is extended or adjusted under 35 U.S.C. 154(b) by 620 days.

(21) Appl. No.: 16/833,653

(22) Filed: Mar. 29, 2020

(65) Prior Publication Data

US 2020/0306012 A1    Oct. 1, 2020

Related U.S. Application Data

(60) Provisional application No. 62/826,828, filed on Mar. 29, 2019.

(51) Int. Cl.
| | |
|---|---|
| G06T 17/00 | (2006.01) |
| G06T 7/10 | (2017.01) |
| G06T 7/00 | (2017.01) |
| A61C 7/00 | (2006.01) |
| G06F 30/10 | (2020.01) |
| G06F 30/27 | (2020.01) |
| G06F 111/16 | (2020.01) |
| G06F 111/04 | (2020.01) |

(52) U.S. Cl.
CPC ............. *A61C 7/002* (2013.01); *G06F 30/10* (2020.01); *G06F 30/27* (2020.01); *G06T 7/0012* (2013.01); *G06T 7/10* (2017.01); *G06T 17/00* (2013.01); *A61C 2007/004* (2013.01); *G06F 2111/04* (2020.01); *G06F 2111/16* (2020.01); *G06T 2207/20112* (2013.01)

(58) Field of Classification Search
None
See application file for complete search history.

(56) References Cited

U.S. PATENT DOCUMENTS

| | | |
|---|---|---|
| 5,975,893 A | 11/1999 | Chishti et al. |
| 6,227,850 B1 | 5/2001 | Chishti et al. |
| 6,227,851 B1 | 5/2001 | Chishti et al. |
| 6,299,440 B1 | 10/2001 | Phan et al. |
| 6,318,994 B1 | 11/2001 | Chishti et al. |
| 6,371,761 B1 | 4/2002 | Cheang et al. |
| 6,386,878 B1 | 5/2002 | Pavlovskaia et al. |
| 6,406,292 B1 | 6/2002 | Chishti et al. |

(Continued)

*Primary Examiner* — Joni Hsu
(74) *Attorney, Agent, or Firm* — Shay Glenn LLP

(57) ABSTRACT

Methods and systems for improving segmentation of a digital model of a patient's dentition into component teeth.

20 Claims, 16 Drawing Sheets
(8 of 16 Drawing Sheet(s) Filed in Color)

(56) References Cited

U.S. PATENT DOCUMENTS

| | | |
|---|---|---|
| 6,409,504 B1 | 6/2002 | Jones et al. |
| 6,457,972 B1 | 10/2002 | Chishti et al. |
| 6,488,499 B1 | 12/2002 | Miller |
| 6,514,074 B1 | 2/2003 | Chishti et al. |
| 6,582,229 B1 | 6/2003 | Miller et al. |
| 6,602,070 B2 | 8/2003 | Miller et al. |
| 6,621,491 B1 | 9/2003 | Baumrind et al. |
| 6,688,886 B2 | 2/2004 | Hughes et al. |
| 6,726,478 B1 | 4/2004 | Isiderio et al. |
| 6,729,876 B2 | 5/2004 | Chishti et al. |
| 6,739,869 B1 | 5/2004 | Taub et al. |
| 6,767,208 B2 | 7/2004 | Kaza |
| 6,783,360 B2 | 8/2004 | Chishti |
| 7,040,896 B2 | 5/2006 | Pavlovskaia et al. |
| 7,063,532 B1 | 6/2006 | Jones et al. |
| 7,074,038 B1 | 7/2006 | Miller |
| 7,074,039 B2 | 7/2006 | Kopelman et al. |
| 7,077,647 B2 | 7/2006 | Choi et al. |
| 7,108,508 B2 | 9/2006 | Hedge et al. |
| 7,134,874 B2 | 11/2006 | Chishti et al. |
| 7,156,661 B2 | 1/2007 | Choi et al. |
| 7,160,107 B2 | 1/2007 | Kopelman et al. |
| 7,241,142 B2 | 7/2007 | Abolfathi et al. |
| 7,293,988 B2 | 11/2007 | Wen |
| 7,309,230 B2 | 12/2007 | Wen |
| 7,357,634 B2 | 4/2008 | Knopp |
| 7,555,403 B2 | 6/2009 | Kopelman et al. |
| 7,637,740 B2 | 12/2009 | Knopp |
| 7,689,398 B2 | 3/2010 | Cheng et al. |
| 7,736,147 B2 | 6/2010 | Kaza et al. |
| 7,746,339 B2 | 6/2010 | Matov et al. |
| 7,844,356 B2 | 11/2010 | Matov et al. |
| 7,844,429 B2 | 11/2010 | Matov et al. |
| 7,865,259 B2 | 1/2011 | Kuo et al. |
| 7,878,804 B2 | 2/2011 | Korytov et al. |
| 7,880,751 B2 | 2/2011 | Kuo et al. |
| 7,904,308 B2 | 3/2011 | Arnone et al. |
| 7,930,189 B2 | 4/2011 | Kuo |
| 7,942,672 B2 | 5/2011 | Kuo |
| 7,970,627 B2 | 6/2011 | Kuo et al. |
| 7,970,628 B2 | 6/2011 | Kuo et al. |
| 8,038,444 B2 | 10/2011 | Kitching et al. |
| 8,044,954 B2 | 10/2011 | Kitching et al. |
| 8,075,306 B2 * | 12/2011 | Kitching ................. A61C 7/00 382/128 |
| 8,092,215 B2 | 1/2012 | Stone-Collonge et al. |
| 8,099,268 B2 | 1/2012 | Kitching et al. |
| 8,108,189 B2 | 1/2012 | Chelnokov et al. |
| 8,126,726 B2 | 2/2012 | Matov et al. |
| 8,260,591 B2 | 9/2012 | Kass et al. |
| 8,275,180 B2 | 9/2012 | Kuo |
| 8,401,826 B2 | 3/2013 | Cheng et al. |
| 8,439,672 B2 | 5/2013 | Matov et al. |
| 8,562,338 B2 | 10/2013 | Kitching et al. |
| 8,591,225 B2 | 11/2013 | Wu et al. |
| 8,788,285 B2 | 7/2014 | Kuo |
| 8,843,381 B2 | 9/2014 | Kuo et al. |
| 8,874,452 B2 | 10/2014 | Kuo |
| 8,896,592 B2 | 11/2014 | Boltunov et al. |
| 8,930,219 B2 | 1/2015 | Trosien et al. |
| 9,037,439 B2 | 5/2015 | Kuo et al. |
| 9,060,829 B2 | 6/2015 | Sterental et al. |
| 9,125,709 B2 | 9/2015 | Matty |
| 9,211,166 B2 | 12/2015 | Kuo et al. |
| 9,220,580 B2 | 12/2015 | Borovinskih et al. |
| 9,364,296 B2 | 6/2016 | Kuo |
| 9,375,300 B2 | 6/2016 | Matov et al. |
| 9,414,897 B2 | 8/2016 | Wu et al. |
| 9,492,245 B2 | 11/2016 | Sherwood et al. |
| 9,642,678 B2 | 5/2017 | Kuo |
| 10,248,883 B2 | 4/2019 | Borovinskih et al. |
| 10,342,638 B2 | 7/2019 | Kitching et al. |
| 10,463,452 B2 | 11/2019 | Matov et al. |
| 10,595,966 B2 | 3/2020 | Carrier, Jr. et al. |
| 10,617,489 B2 | 4/2020 | Grove et al. |
| 10,722,328 B2 | 7/2020 | Velazquez et al. |
| 10,758,322 B2 | 9/2020 | Pokotilov et al. |
| 10,779,718 B2 | 9/2020 | Meyer et al. |
| 10,792,127 B2 | 10/2020 | Kopelman et al. |
| 10,828,130 B2 | 11/2020 | Pokotilov et al. |
| 10,835,349 B2 | 11/2020 | Cramer et al. |
| 10,973,611 B2 | 4/2021 | Pokotilov et al. |
| 10,996,813 B2 | 5/2021 | Makarenkova et al. |
| 10,997,727 B2 | 5/2021 | Xue et al. |
| 11,020,205 B2 | 6/2021 | Li et al. |
| 11,020,206 B2 | 6/2021 | Shi et al. |
| 11,026,766 B2 | 6/2021 | Chekh et al. |
| 11,033,359 B2 | 6/2021 | Velazquez et al. |
| 11,071,608 B2 | 7/2021 | Derakhshan et al. |
| 11,096,763 B2 | 8/2021 | Akopov et al. |
| 11,116,605 B2 | 9/2021 | Nyukhtikov et al. |
| 11,147,652 B2 | 10/2021 | Mason et al. |
| 11,151,753 B2 | 10/2021 | Gao et al. |
| 11,259,896 B2 | 3/2022 | Matov et al. |
| 2003/0008259 A1 | 1/2003 | Kuo et al. |
| 2003/0143509 A1 | 7/2003 | Kopelman et al. |
| 2003/0207227 A1 | 11/2003 | Abolfathi |
| 2004/0137400 A1 | 7/2004 | Chishti et al. |
| 2004/0152036 A1 * | 8/2004 | Abolfathi ................. A61C 7/00 433/24 |
| 2004/0197728 A1 | 10/2004 | Abolfathi et al. |
| 2004/0259049 A1 | 12/2004 | Kopelman et al. |
| 2005/0182654 A1 | 8/2005 | Abolfathi et al. |
| 2005/0244791 A1 | 11/2005 | Davis et al. |
| 2006/0127836 A1 | 6/2006 | Wen |
| 2006/0127852 A1 | 6/2006 | Wen |
| 2006/0127854 A1 | 6/2006 | Wen |
| 2006/0275731 A1 | 12/2006 | Wen et al. |
| 2006/0275736 A1 | 12/2006 | Wen et al. |
| 2006/0282288 A1 * | 12/2006 | Rodriguez ....... G06Q 10/06375 705/2 |
| 2008/0306724 A1 | 12/2008 | Kitching et al. |
| 2010/0009308 A1 | 1/2010 | Wen et al. |
| 2010/0039296 A1 * | 2/2010 | Marggraff ........... G06F 3/03545 341/20 |
| 2010/0068672 A1 | 3/2010 | Arjomand et al. |
| 2010/0068676 A1 | 3/2010 | Mason et al. |
| 2010/0092907 A1 | 4/2010 | Knopp |
| 2010/0167243 A1 | 7/2010 | Spiridonov et al. |
| 2013/0204599 A1 | 8/2013 | Matov et al. |
| 2013/0308846 A1 * | 11/2013 | Chen ..................... G06T 7/0012 382/131 |
| 2014/0177911 A1 | 6/2014 | Heisele |
| 2016/0310235 A1 | 10/2016 | Derakhshan et al. |
| 2017/0065379 A1 * | 3/2017 | Cowburn ................ G06F 3/015 |
| 2017/0076443 A1 * | 3/2017 | Ye ........................ A61B 5/4547 |
| 2017/0169562 A1 * | 6/2017 | Somasundaram ... G06V 10/454 |
| 2017/0273760 A1 | 9/2017 | John et al. |
| 2018/0280118 A1 | 10/2018 | Cramer |
| 2019/0029784 A1 | 1/2019 | Moalem et al. |
| 2019/0053876 A1 | 2/2019 | Sterental et al. |
| 2019/0192259 A1 | 6/2019 | Kopelman et al. |
| 2019/0328487 A1 | 10/2019 | Levin et al. |
| 2019/0328488 A1 | 10/2019 | Levin et al. |
| 2019/0333622 A1 | 10/2019 | Levin et al. |
| 2019/0343601 A1 | 11/2019 | Roschin et al. |
| 2020/0000552 A1 | 1/2020 | Mednikov et al. |
| 2020/0000554 A1 | 1/2020 | Makarenkova et al. |
| 2020/0000555 A1 | 1/2020 | Yuryev et al. |
| 2020/0085546 A1 | 3/2020 | Li et al. |
| 2020/0107915 A1 | 4/2020 | Roschin et al. |
| 2020/0155274 A1 | 5/2020 | Pimenov et al. |
| 2020/0214800 A1 | 7/2020 | Matov et al. |
| 2020/0297458 A1 | 9/2020 | Roschin et al. |
| 2020/0306011 A1 | 10/2020 | Chekhonin et al. |
| 2020/0315744 A1 | 10/2020 | Cramer |
| 2020/0360109 A1 | 11/2020 | Gao et al. |
| 2021/0073998 A1 | 3/2021 | Brown et al. |
| 2021/0134436 A1 | 5/2021 | Meyer et al. |
| 2021/0174477 A1 | 6/2021 | Shi et al. |
| 2021/0322136 A1 * | 10/2021 | Anssari Moin ....... A61C 9/0053 |
| 2022/0084205 A1 * | 3/2022 | Jin ........................... G06T 7/11 |

* cited by examiner

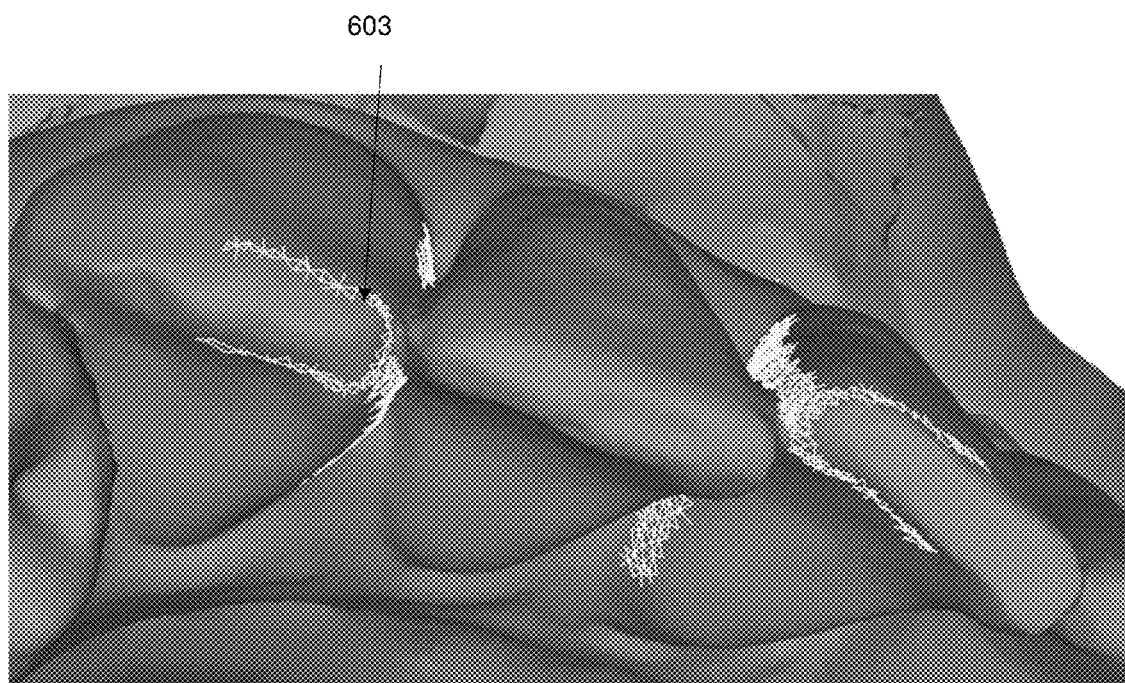
FIG. 6B
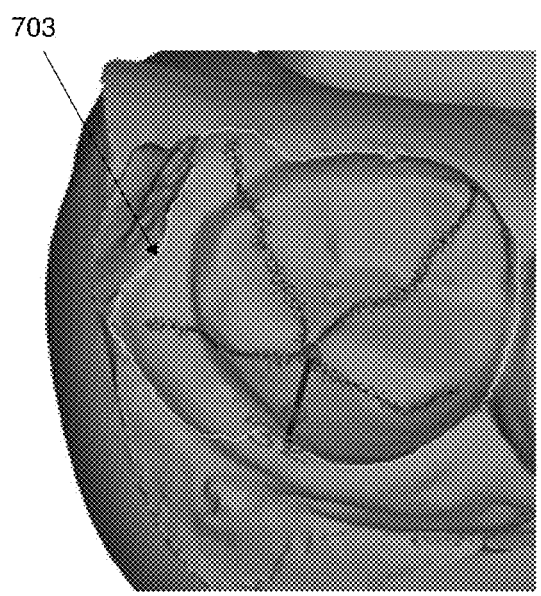 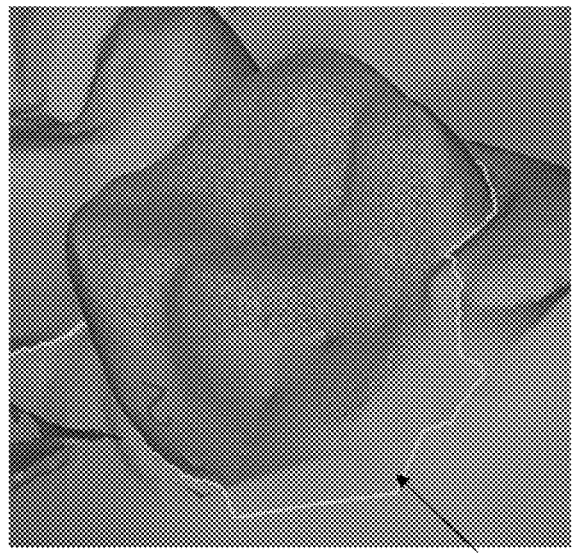
FIG. 7A  FIG. 7B

SEGMENTATION QUALITY ASSESSMENT

CLAIM OF PRIORITY

This patent application claims priority to U.S. Provisional Patent Application No. 62/826,828, called "SEGMENTATION QUALITY ASSESSMENT," filed on Mar. 29, 2019, herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods and systems described herein relate to the field of computer-assisted dentistry and orthodontics.

BACKGROUND

Two-dimensional (2D) and three-dimensional (3D) digital image technology may be used to assist in dental and orthodontic treatment, including forming a digital model of a patient's dentition. Such models may be particularly useful, among other things, in developing an orthodontic treatment plan for the patient, as well as in creating one or more orthodontic appliances to implement the treatment plan. In particular, digital models of the patient's dentition may be particularly useful when they are accurately divided up into dental components such as individual teeth. This process may be referred to as segmentation of the teeth.

Unfortunately, it may be difficult to accurately segment a digital model into individual teeth. It would be beneficial to provide techniques and systems for segmenting a digital model and/or for checking the accuracy of segmented digital models.

SUMMARY OF THE DISCLOSURE

Described herein are methods and systems for improving segmentation of a digital model of a patient's dentition into component teeth, gingiva, etc.

For example, described herein are computer-implemented method for more accurately establishing a segmentation boundary between a tooth and the gingiva. A computer-implemented method may include: determining, for a tooth of a digital model, a first restriction boundary for the tooth; generating a loop path around a surface of the digital model of the tooth based on the first restriction boundary; estimating a loop path metric from the loop path; adjusting the first restriction boundary by iteratively expanding the restriction boundary in a first direction and generating a new loop path based on the expanded restriction boundary until a second loop path metric that is estimated from the new loop path no longer improves; repeating the step of adjusting the first restriction boundary for one or more additional directions; and segmenting the digital model of the tooth based on a final adjusted first restriction boundary.

Segmenting the digital model of the tooth based on a final adjusted first restriction boundary may include segmenting the digital model of the tooth between the tooth and the gingiva.

Any of these methods may include estimating the first restriction boundary for the tooth based on one or more of: a facial plane of the clinical crown (FPCC), a middle plane of the clinical crown (MPCC), a plane orthogonal to a Z-axis of the tooth (HPCC), a facial axis of the clinical crown (FACC) curve, an FACC gingival point, an FACC buccal point, and a central plane of the clinical crown (CPCC).

For example, a computer-implemented method may comprise: determining, for a tooth of a digital model, a first restriction boundary for the tooth based on one or more of: a facial plane of the clinical crown (FPCC), a middle plane of the clinical crown (MPCC), a plane orthogonal to a Z-axis of the tooth (HPCC), a facial axis of the clinical crown (FACC) curve, an FACC gingival point, an FACC buccal point, and a central plane of the clinical crown (CPCC); generating a loop path around a surface of the digital model of the tooth based on the first restriction boundary; estimating a loop path metric from the loop path; adjusting the first restriction boundary by iteratively expanding the restriction boundary in a first direction and generating a new loop path based on the expanded restriction boundary until a second loop path metric that is estimated from the new loop path no longer improves; repeating the step of adjusting the first restriction boundary for one or more additional directions; and segmenting the digital model of the tooth between the tooth and the gingiva based on a final adjusted first restriction boundary.

The methods described herein may include confirming that the restriction boundary is faulty, e.g., before beginning the method.

The loop path metric comprises a path curvature for the loop path or the new loop path. For example, the loop path metric may comprise a mean or variance of the path curvature for the loop path or the loop path metric. The loop path metric may comprise a length of any convex edges of the loop path.

In any of these methods, the first restriction boundary may be adjusted until the second loop path metric is larger than a loop path metric prior to expanding the restriction boundary.

Any of the methods described herein may be performed by an apparatus configured or adapted to perform them. For example, a system for more accurately establishing a boundary between a tooth and the gingiva may include: one or more processors; a memory coupled to the one or more processors, the memory configured to store computer-program instructions, that, when executed by the one or more processors, perform a computer-implemented method comprising: determining, for a tooth of a digital model, a first restriction boundary for the tooth; generating a loop path around a surface of the digital model of the tooth based on the first restriction boundary; estimating a loop path metric from the loop path; adjusting the first restriction boundary by iteratively expanding the restriction boundary in a first direction and generating a new loop path based on the expanded restriction boundary until a second loop path metric that is estimated from the new loop path no longer improves; repeating the step of adjusting the first restriction boundary for one or more additional directions; and segmenting the digital model of the tooth based on a final adjusted first restriction boundary.

Also described herein are computer-implemented methods for determining the accuracy of segmentation in one or a group of segmented digital models of a patient's teeth. For example, described herein are computer-implemented methods comprising: applying a plurality of filters to check the segmentation of a segmented digital model of a patient's dentition; ranking the segmentation of the segmented digital model of the patient's dentition based on the results of the plurality of filters; and automatically processing the segmented digital model of the patient's dentition if the segmentation of the segmented digital model of the patient's dentition is ranked meets a threshold rank.

For example, a computer-implemented method may include: applying a plurality of filters to check the segmentation of a segmented digital model of a patient's dentition; ranking the segmentation of the segmented digital model of the patient's dentition based on the results of the plurality of filters; and automatically processing the segmented digital model of the patient's dentition if the segmentation of the segmented digital model of the patient's dentition is ranked meets a threshold rank, otherwise re-processing the segmentation of the segmented digital model of the patient's dentition and generating a report and presenting the report to a user or technician.

In any of these methods automatically processing may comprise automatically processing the segmented digital model of the patient's dentition if the segmentation of the segmented digital model of the patient's dentition is ranked meets a threshold rank, otherwise re-processing the segmentation of the segmented digital model of the patient's dentition.

Any of these methods may include generating a report and presenting the report to a user or technician.

The plurality of filters may comprises one or more filters configured to check one or more of: segmented tooth shape, tooth count, segmented tooth position, segmented surface boundaries, missing teeth, extra teeth, segmented tooth crown shape, segmented tooth crown orientation, space between segmented teeth, segmented tooth surface curvature, segmented gingival border, trimmed teeth, tooth numbering, visible top of crown, and holes in segmentation. For example, at least some of the filters may comprise machine learning filters (machine learning agents). Any of these methods may include training the machine-learning filters against both positive groups that are well segmented and negative groups that are poorly segmented.

Ranking the segmentation of the segmented digital model of the patient's dentition based on the results of the plurality of filters may comprise averaging a numerical score from each of the filters of the plurality of filters.

Automatically processing the segmented digital model of the patient's dentition if the segmentation of the segmented digital model of the patient's dentition is ranked meets the threshold rank may comprise automatically processing the segmented digital model if the rank of the segmented digital model is greater than the threshold rank.

As mentioned above, any of the methods described herein may be configured as a system to perform the method. For example, a system for determining the accuracy of segmentation in one or a group of segmented digital models of a patient's teeth may include: one or more processors; a memory coupled to the one or more processors, the memory configured to store computer-program instructions, that, when executed by the one or more processors, perform a computer-implemented method comprising: applying a plurality of filters to check the segmentation of a segmented digital model of a patient's dentition; ranking the segmentation of the segmented digital model of the patient's dentition based on the results of the plurality of filters; and automatically processing the segmented digital model of the patient's dentition if the segmentation of the segmented digital model of the patient's dentition is ranked meets a threshold rank.

Also described herein are methods for determining the accuracy of segmentation in one or a group of segmented digital models of a patient's teeth based on color. For example, a computer-implemented method may include: identifying one or more outlying regions of the segmented digital model of the patient's dentition having tooth-like color that are outside of any region of the segmented digital model of the patient's dentition that is indicated as teeth; estimating a probability that any of the one or more outlying regions are teeth; scoring the segmentation of the segmented digital model of the patient's dentition based, at least in part, on the probability that any of the one or more outlying regions are teeth; and reprocessing the segmented digital model of the patient's dentition if the score of the segmented digital model of the patient's dentition is outside of a passing range.

For example, a computer-implemented method may include: determining a color quality of a segmented digital model of a patient's dentition; identifying one or more outlying regions of the segmented digital model of the patient's dentition having tooth-like color that are outside of any region of the segmented digital model of the patient's dentition that is indicated as teeth; estimating a probability that any of the one or more outlying regions are teeth; scoring the segmentation of the segmented digital model of the patient's dentition based, at least in part, on the probability that any of the one or more outlying regions are teeth; and reprocessing the segmented digital model of the patient's dentition if the score of the segmented digital model of the patient's dentition is outside of a passing range, generating a report, and presenting the report to a user or technician.

Thus, any of these methods may include determining a color quality of a segmented digital model of a patient's dentition, and my further include stopping the method if the color quality is below a color quality metric.

The methods described herein may include outputting a grade or score of the segmented digital model of the patient's dentition (including delivering the grade or score to a user, such as a doctor, dentist, orthodontist, etc., and/or a technician). The technician may then process and re-segment the digital model of the patient's dentition.

Any of these methods may include adjusting the score of the segmentation of the segmented digital model of the patient's dentition based on a comparison between the color values of the segmentation boundary and the color value on either sides of the segmentation boundary.

Identifying one or more outlying regions of the segmented digital model of the patient's dentition having tooth-like color may include identifying the one or more outlying region having tooth-like blue and green color values.

Estimating the probability may comprise basing the probability on at least one or more of: the size of the outlying region, the relative boundary size of the outlying region, the presence or absence of a cusp on the outlying region, the presence of sharp edges on the outlying region and the shape of the outlying region.

As mentioned, any of the methods described herein may be configured as a system to perform the method. For example, a system for determining the accuracy of segmentation in one or a group of segmented digital models of a patient's teeth based on color may include: one or more processors; and a memory coupled to the one or more processors, the memory configured to store computer-program instructions, that, when executed by the one or more processors, perform a computer-implemented method comprising: identifying one or more outlying regions of the segmented digital model of the patient's dentition having tooth-like color that are outside of any region of the segmented digital model of the patient's dentition that is indicated as teeth; estimating a probability that any of the one or more outlying regions are teeth; scoring the segmentation of the segmented digital model of the patient's dentition based, at least in part, on the probability that any of the one or more outlying regions are teeth; and reprocessing the segmented digital model of the patient's dentition if the score of the segmented digital model of the patient's dentition is outside of a passing range.

BRIEF DESCRIPTION OF THE DRAWINGS

The patent or application file contains at least one drawing executed in color. Copies of this patent or patent application publication with color drawings will be provided by the Office upon request and payment of the necessary fee.

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 6A and 6B shows examples of boundary restriction based on the edges from a neighboring tooth in a buccal and lingual view, respectively.

FIGS. 7A and 7B illustrate examples of restriction faults.

DETAILED DESCRIPTION

Figure 1:
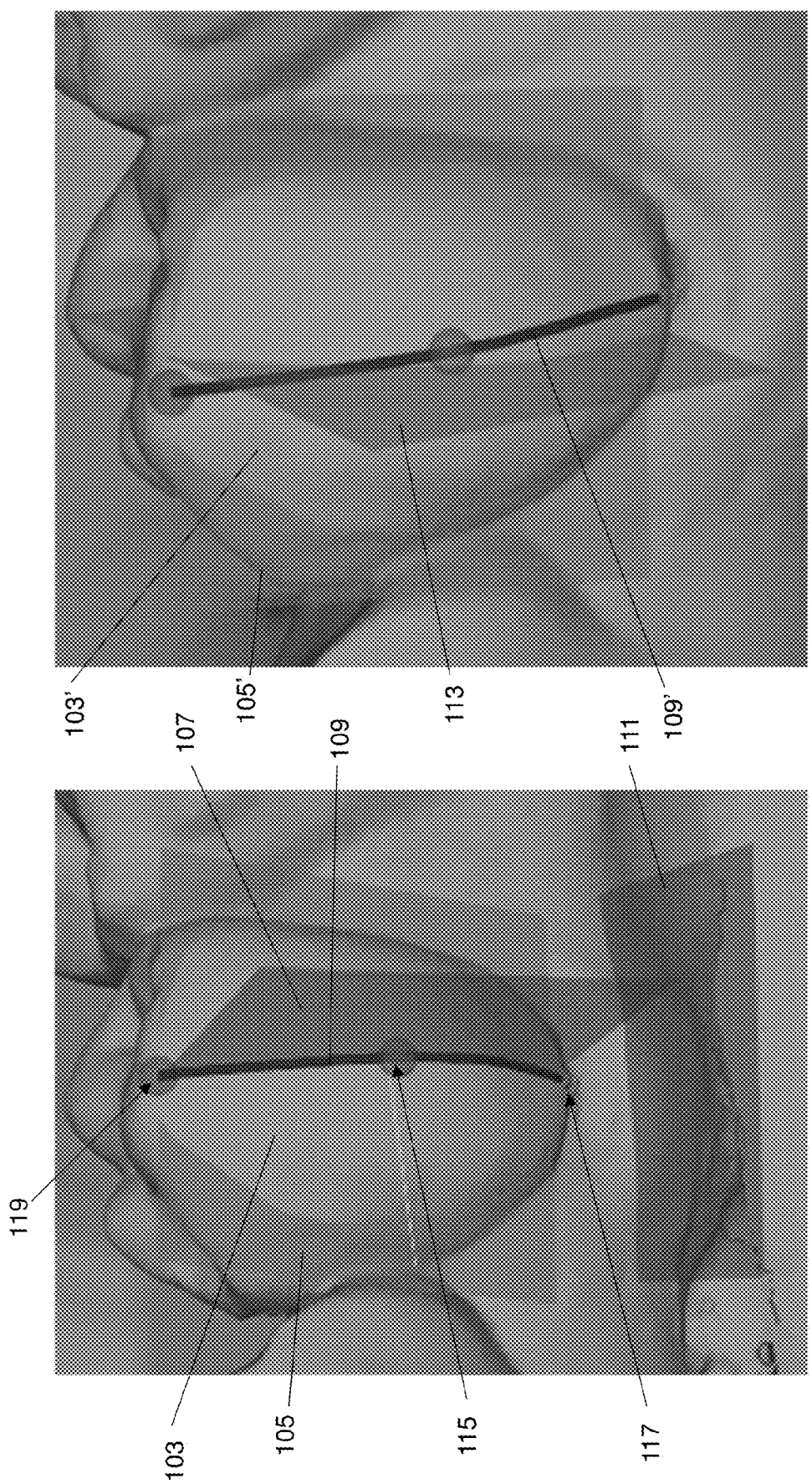
FIGS. 1A and 1B illustrate the arrangement of planes, points and surface lines on an example of a tooth as described herein.

Described herein are methods and apparatuses (e.g., systems, including computing device readable media, and devices) for segmenting a digital model of a patient's dental arch into individual dental features, such as teeth, gingiva, lips, cheek, etc. In particular, described herein are methods for improving segmentation and identification of individual components using an automated techniques and apparatuses. These methods and apparatuses solve technical problems related to the design and segmentation of images and/or models of a patient's arch, including properly numbering the teeth of the patient's arch to account for the missing or ectopic teeth.

The methods and apparatuses described herein may be useful in planning and fabrication of dental appliances, including elastic polymeric positioning appliances, is described in detail in U.S. Pat. No. 5,975,893, and in published PCT application WO 98/58596, which is herein incorporated by reference for all purposes. Systems of dental appliances employing technology described in U.S. Pat. No. 5,975,893 are commercially available from Align Technology, Inc., San Jose, Calif., under the tradename, Invisalign System.

Throughout the body of the Description of Embodiments, the use of the terms "orthodontic aligner", "aligner", or "dental aligner" is synonymous with the use of the terms "appliance" and "dental appliance" in terms of dental applications. For purposes of clarity, embodiments are hereinafter described within the context of the use and application of appliances, and more specifically "dental appliances."

The methods and apparatuses (e.g., systems, devices, etc.) described below can be used with and/or integrated into an orthodontic treatment plan. The methods and apparatuses described herein may be used to segment a patient's teeth from a two-dimensional image and this segmentation information may be used to simulate, modify and/or choose between various orthodontic treatment plans. Segmenting the patient's teeth can be done automatically (e.g., using a computing device). For example, segmentation can be performed by a computing system automatically by evaluating data (such as a two-dimensional photo, a scan, or a dental impression) of the patient's teeth or arch.

As described herein, a two-dimensional image can be taken of a patient's teeth with a camera. The patient can be positioned in front of the camera and asked to smile to allow the image to capture the natural smile of the patient, including the visible teeth, gingiva, and lips of the patient. Multiple images of the patient's teeth can be taken to ensure the smile and teeth of the patient are captured and in focus. In some variations a digital scan of the patient's teeth may be taken by capturing a large number of images. After capturing the image(s), the image(s) can be pre-processed by the computing device to find the midline of the patient's teeth and rotate the image until the midline is vertical.

For example, an intraoral scanner may image a patient's dental arch and generate a virtual three-dimensional model of that dental arch. During an intraoral scan procedure (also referred to as a scan session), a user (e.g., a dental practitioner) of an intraoral scanner may generate multiple different images (also referred to as scans or medical images) of a dental site, model of a dental site, or other object. The images may be discrete images (e.g., point-and-shoot images) or frames from a video (e.g., a continuous scan). The images can be preprocessed by the computing device as described above to find the midline and rotate the images until the midline is vertical.

An automated tooth segmentation system may use automated agents to identify and/or number individual teeth and/or dental features of virtual representations of teeth, such as teeth represented in a two-dimensional photographic image or a 3D dental mesh model resulting from a digital scan.

There are a variety of methods for computer-implemented segmentation, including feature skeleton analysis and two-dimensional (2D) slice analysis.

For example, feature skeleton analysis may form a volumetric representation of the dentition model to model individual teeth by identifying a core of voxels that forms a skeleton for the dentition. The skeleton is divided into branches, each containing voxels that lie entirely within one tooth. One technique for identifying the branches is by defining a plane that cuts through the skeleton roughly parallel to the occlusal plane of the patient's dentition ("horizontal plane"). Each branch intersects the horizontal plane at one or more points, or clusters, that are relatively distant from the clusters associated with the other branches. The computer forms the individual tooth models by linking other voxels to the appropriate branches of the skeleton.

2D slice analysis may involve dividing the voxel representation of the dentition model into a series of parallel 2D planes, or slices, that are each one voxel thick and that are roughly parallel to the dentition's occlusal plane, which is roughly normal to the model's z-axis. Each of the 2D slices includes a 2D cross section of the dentition, the surface of which represents the lingual and buccal surfaces of the patient's teeth and/or gums. The computer inspects the cross section in each 2D slice to identify voxels that approximate the locations of the interproximal margins between the teeth. These voxels lie at the tips of cusps in the 2D cross-sectional surface. The computer then uses the identified voxels to create 3D surfaces intersecting the dentition model at these locations. The computer segments the dentition model along these intersecting surfaces to create individual tooth models.

For example, the computer may begin by identifying the voxels that form each of the 2D slices. The computer then identifies, for each 2D slice, the voxels that represent the buccal and lingual surfaces of the patient's teeth and gums and defines a curve that includes all of these voxels. This curve represents the surface of the 2D cross section. The computer then calculates the rate of curvature (e.g., the derivative of the radius of curvature) at each voxel on the 2D cross-sectional surface and identifies all of the voxels at which local maxima in the rate of curvature occur. Each voxel at which a local maximum occurs represents a "cusp" in the 2D cross-sectional surface and roughly coincides with an interproximal margin between teeth. In each 2D slice, the computer identifies pairs of these cusp voxels that correspond to the same interproximal margin, and the computer labels each pair to identify the interproximal margin with which it is associated. The computer then identifies the voxel pairs on all of the 2D slices that represent the same interproximal margins. For each interproximal margin, the computer fits a 3D surface approximating the geometry of the interproximal margin among the associated voxel pairs. The computer may create a 3D surfaces that represent the interproximal regions. All of the voxels that lie between adjacent ones of these 3D surfaces represent an individual tooth.

Automated segmentation may be enhanced through a technique known as "seed cusp detection." The term "seed cusp" refers to a location at which an interproximal margin between adjacent teeth meets the patient's gum tissue. In a volumetric representation of the patient's dentition, a seed cusp for a particular interproximal margin may be found at the cusp voxel that lies closest to the gum line. By applying the seed cusp detection technique to the 2D slice analysis, the computer may identify all of the seed cusp voxels in the 3D model automatically.

In one particular implementation of the seed cusp detection technique the computer detects the seed cusps by identifying each 2D slice in which the rate of curvature of a cusp first falls below a predetermined threshold value. The computer begins by selecting a 2D slice that intersects all of the teeth in the arch. The computer attempts to select a slice that is near the gingival regions but that does not include any voxels representing gingival tissue. The computer then identifies all of the cusp voxels in the 2D slice. If the rate of curvature of the 2D cross section at any of the cusp voxels is less than a predetermined threshold value, the computer labels that voxel as a seed cusp. The computer then selects the next 2D slice, which should be one voxel layer closer to the gingival region, and identifies all of the cusp voxels that are not associated with a cusp for which the computer has already identified a seed cusp. If the rate of curvature of the 2D cross section is less than the predetermined threshold value at any of these cusp voxels, the computer labels the voxel as a seed cusp and proceeds to the next 2D slice. The computer continues in this manner until a seed cusp voxel has been identified for each cusp associated with an interproximal margin.

Tooth-Gingival Boundary Identification

In any of the segmentation methods and apparatuses described herein, a technique and/or agent for identifying the tooth-gingival boundary may be used.

Errors may occur during tooth segmentation on 3D scan surface, particularly errors in which tooth to gingival bounds are not precisely determined. Typical problems may include marking gingiva as tooth crown, missing tooth gingival recession regions, and the like. Such imprecision may lead to incorrect tooth shape modeling, which may impact patient care.

For example in some variations, segmentation may include the use of heuristic rules that mark regions on a scan surface which may restrict tooth crown boundaries. The form and positions of such marked regions may depend on parameters, some or all of which may be calculated statistically for each tooth dental type, including from population data. Often these parameters do not fit well for teeth with non-regular shape. The parameters themselves may be less reliable, particularly where the tooth dental type was evaluated incorrectly before segmentation.

Described herein are methods and apparatuses (including automated systems) for identifying tooth-gingival boundaries that may avoid these problems, and may be part of a segmentation technique. These methods and apparatuses may be referred to as "backtracking" (or segmentation backtracking) methods and apparatuses and may generally adapt and apply parameters that are associated with a specific tooth shape, and may allow the use of more restriction regions enhancing accuracy. The segmentation backtracking techniques described herein may be used to more accurately and computationally stably establish a boundary between tooth and gingiva, particularly for a variety of tooth shapes variations (e.g., variations in size, form, cusp positions and count).

The segmentation backtracking methods and apparatuses configured to perform them may be an improvement in tooth segmentation method based on surface curvature. In general a segmentation backtracking method may find the shortest separating loop around a tooth that passes through the edge closest to the facial axes of the clinical crown (FACC) gingival point. Once identified, the defined inner area may be "flooded," and a length metric of the edge may be determined. The length metric of the edge may depend on the tooth type, surface curvature at the edge bounds, the Euclid length, and/or belonging to the set of restriction edges.

The middle point between an FACC occlusal and gingival points may be referred to as the MPCC point (e.g., MPCC refers to the middle plane of the clinical crown). See, e.g., U.S. Pat. No. 8,126,726 for a description of the FACC and MPCC. For each tooth, tooth auxiliary planes may be calculated, including: the facial plane of the clinical crown (FPCC), which contains the MPCC; the MPCC, which contains the FACC curve and usually bisects the tooth (generally, a line normal to the MPCC is directed toward teeth with larger diameter (ID); an HPCC plane, which is orthogonal to the Z-axis of the particular tooth and includes more gingival than gum points; and a central plane of the clinical crown (CPCC), which has a normal vector that points along the jaw line at this place and passes through the MPCC point. These auxiliary planes are illustrated in FIGS. 1A-1B. FIG. 1A shows a buccal view of one example of a digital model of a tooth 103 onto which the facial plane of the clinical crown (FPCC) 105 is shown; normal to this plane is the middle plane of the clinical crown (MPCC) 107. The intersection between the MPCC and the surface of the tooth is the FACC curve 109. In FIG. 1A the MPCC point 115 is on the PACC curve and is midway between an occlusal point in the FPCC plane (the FACC occlusal point 119) and a gingival point on the FPCC plane (the FACC gingival point 117). The HPCC plane 111 underlies the crown region (in the gingiva) and is orthogonal to the z-axis of the tooth, as shown.

FIG. 1B is another dental scan showing a buccal view of another tooth 105' onto which an FPCC 105' and a central plane of the clinical crown 113 (CPCC) is shown. An FACC curve 109' is also shown in FIG. 1B. The FACC occlusal point 119', FACC gingival point 117' and the MPCC point 115' are all shown as well.

Figure 2:
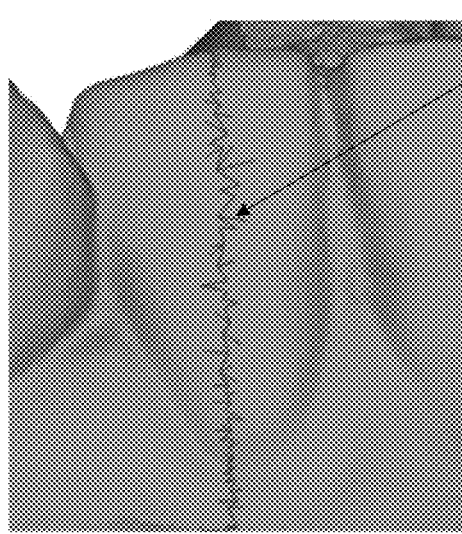
FIG. 2 shows an example of a restriction boundary (red zone) on the buccal side of a tooth.
Figure 3:
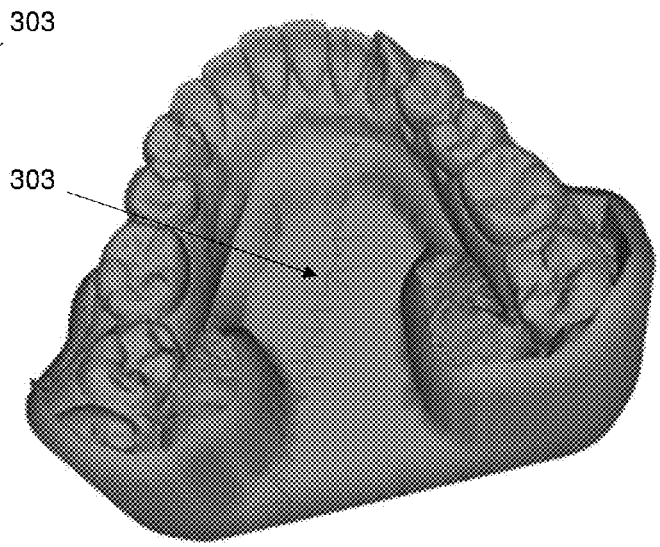
FIG. 3 shows the restriction boundary of FIG. 2 on the lingual side of the tooth.

As mentioned above, a variety of boundary restrictions may be applied. For example, FIGS. 2-3, 4A-4B, and 5A-5B illustrate boundary restrictions that may be used when identifying the tooth-gingival boundary as described above. FIGS. 2-3 illustrate a restriction boundary, referred to herein as a "red zone" 203 formed through the MPCC in a region in which the MPCC is closer to the FPCC than some predetermined distance. FIG. 2, shows an exemplary red zone restriction from the buccal side, while FIG. 3 shows a red zone restriction from the lingual side. The restriction is shown on the surface of the digital model of the teeth and may be estimated from the planes and/or points (e.g., FPCC, MPCC, HPCC, FACC curve, FACC gingival point, FACC buccal point, and/or CPCC, etc.) estimated from the digital model of the teeth. Note that this technique may be applied to an unsegmented, partially or initially segmented digital model of a patient's dentition. In particular, the methods and apparatuses described herein may be used in an initially segmented digital model in order to refine or improve the segmentation, and particularly the tooth-gingiva boundary.

Figure 4:
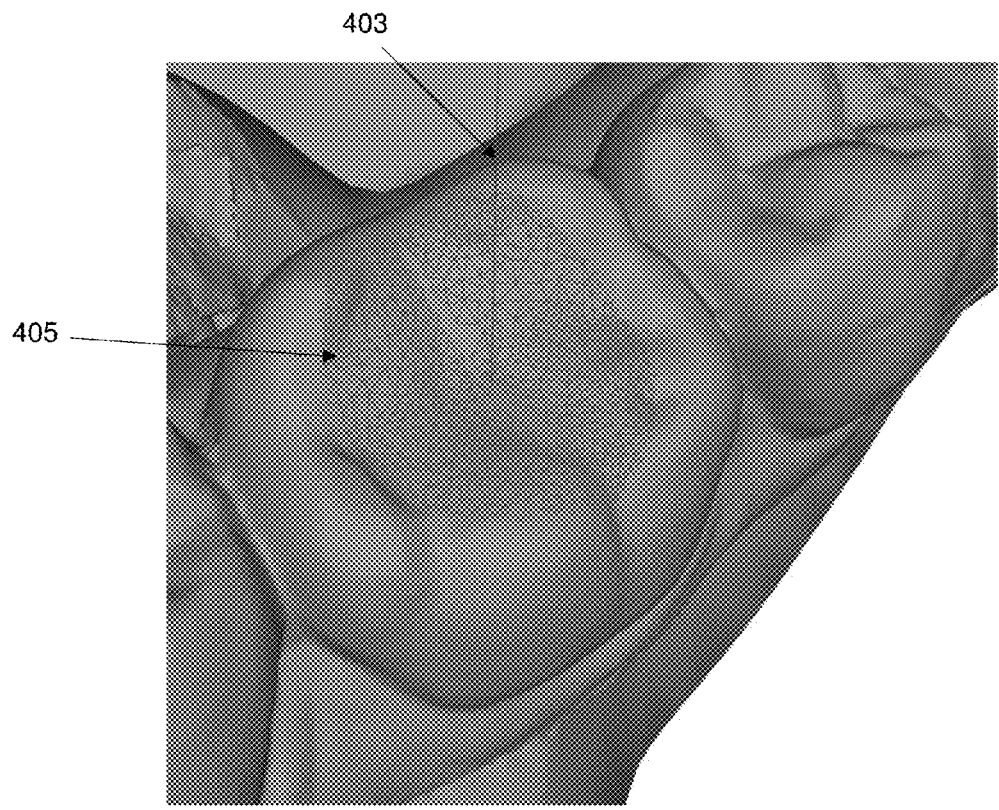
FIG. 4 illustrates another boundary, shown as a cylindrical boundary on molar.

FIG. 4 illustrates another boundary, shown as a cylindrical boundary on molar. In FIG. 4, the edges of a cylinder for molar teeth are determined for a surface region of the molar within a cylinder having a central axis for the cylinder that is forms at the intersection of the MPCC plane and a shifted FPCC plane. Traversing edges may start from a central point. The central point is on the one of the edges from the red zone that intersects the shifted FPCC plane. In FIG. 4, the edges from the FACC occlusal point to the gap are taken into account. In FIG. 4, the cylindrical restriction surface region 405 is centered on the axis 403.

Figure 5A:
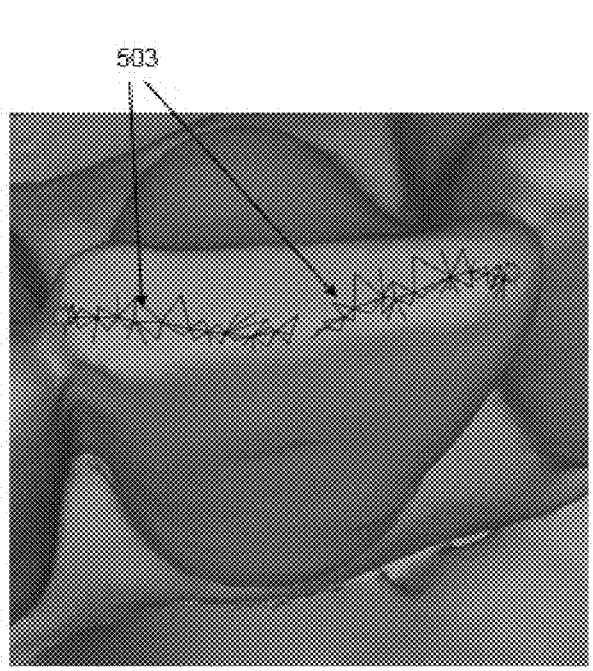
FIG. 5A illustrates and example of boundary restrictions formed through an FACC occlusal point on the cusp of a tooth.
Figure 5B:
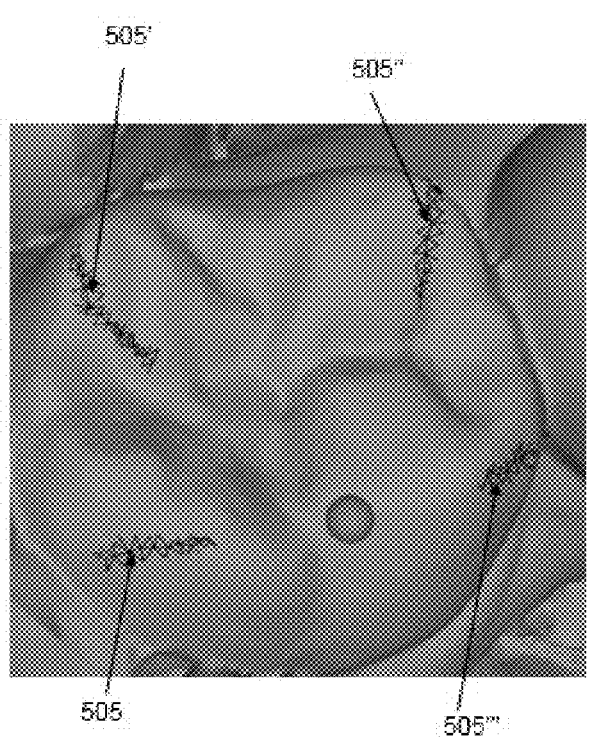
FIG. 5B shows another example of boundary restrictions formed through an FACC occlusal point on the cusp of a tooth (e.g., molar).

In some variations, a boundary may be formed from cusps from the FACC occlusal point (filter lines). This is illustrated in FIG. 5A, showing the lines to the cusps 503 for an example of an anterior tooth. The cusp points may be detected as extreme vertices fitted on the tooth model along fixed directions, as shown. Similarly, FIG. 5B shows cusp points forming a boundary 505, 505', 505", 505'" on the surface of a molar.

Figure 6A:
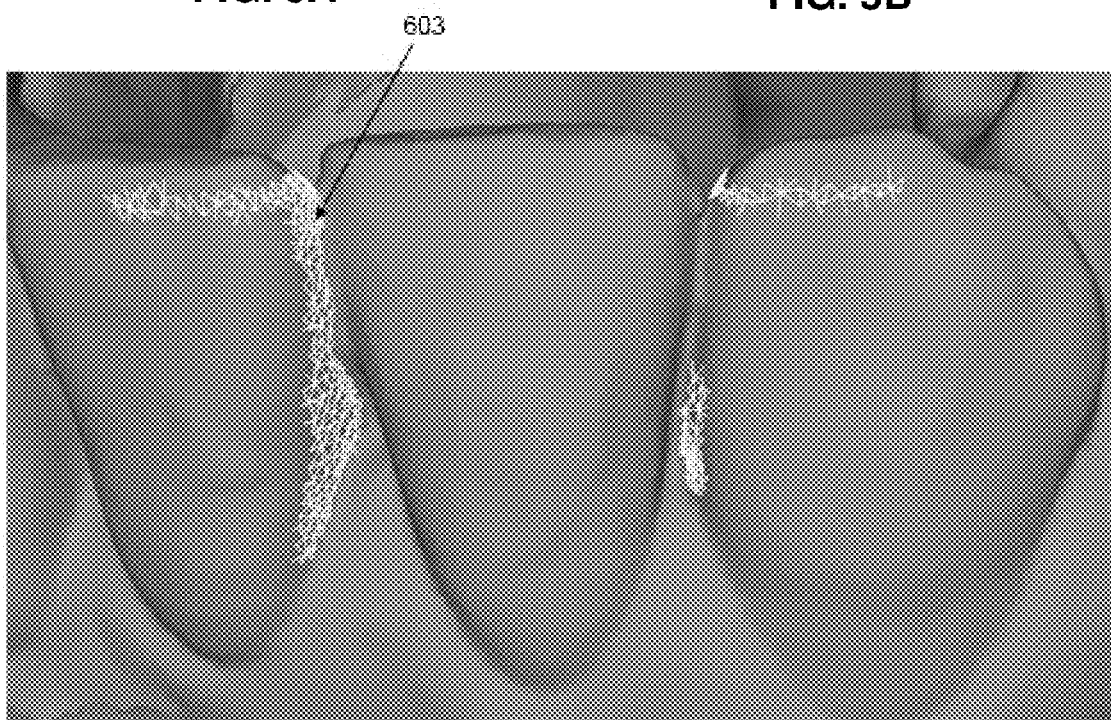

Boundaries may also be set based on the edges from a neighboring tooth. For example, as shown in FIGS. 6A-6B, selected edges which are normal-directed relative to the current tooth CPCC plane may be determined, and a boundary may be identified by traversing from a previously selected edges to edges that intersect with a plane collinear to the HPCC and pass through center of a start edge. Traversing may continue if it is moving away from the MPCC plane. If traversing in both directions around tooth is successful, then all line 603 is filtered. FIG. 6A shows a buccal view and FIG. 6B shows an occlusal view.

As mentioned above, if the boundaries, which may be determined heuristically, do not fit a particular digital scan well, this may result in a restriction fault. A restriction fault occurs when the restriction region extends beyond the borders of the tooth, e.g., into the gingiva and/or other structures. This is illustrated in FIGS. 7A and 7B, showing examples of restriction faults. In FIG. 7A the identified restriction region and resulting loop path 703 extends well beyond the likely tooth border and into the gingiva. Similarly in FIG. 7B, the loop path 703' also extends beyond the likely tooth border.

The segmentionat backtracing method and apparatuses described herein may prevent or reduce problems with restrictions faults. In general, segmentation backtracking may, either in every case or when restriction faults are detected, reduce the initial restrictions and iteratively expand the selected restriction (in one or more directions) and recalculate a bounding loop that may then reviewed by determining one or more metric for the new bounding loop. The expansion of the selected restriction, determining the new loop path and comparing the new loop path metric to the prior lop path metric may be repeated until the boundary loop is optimized according to the metric, or some function of multiple metrics, e.g., average, sum, etc.

Any appropriate metric may be used to check the loop path. In general, loop path values might be compared with some threshold or with values of current record path. Examples of metrics that may be used may include: path curvature for one or more of: all paths, new segment, removed segment; mean, variance, etc. The metric may be the length of convex edges of the loop path. In some variations the loop path metric includes the distance from current restriction line to new path segment. In some variations, the loop path includes area of faces inside crown with edges marked as edges of neighbor tooth (filtered by normal), and/or projections to HPCC plane "roundness," which may be calculated as the square of the perimeter, divided by the area (where lower values are typically better).

Figure 8:
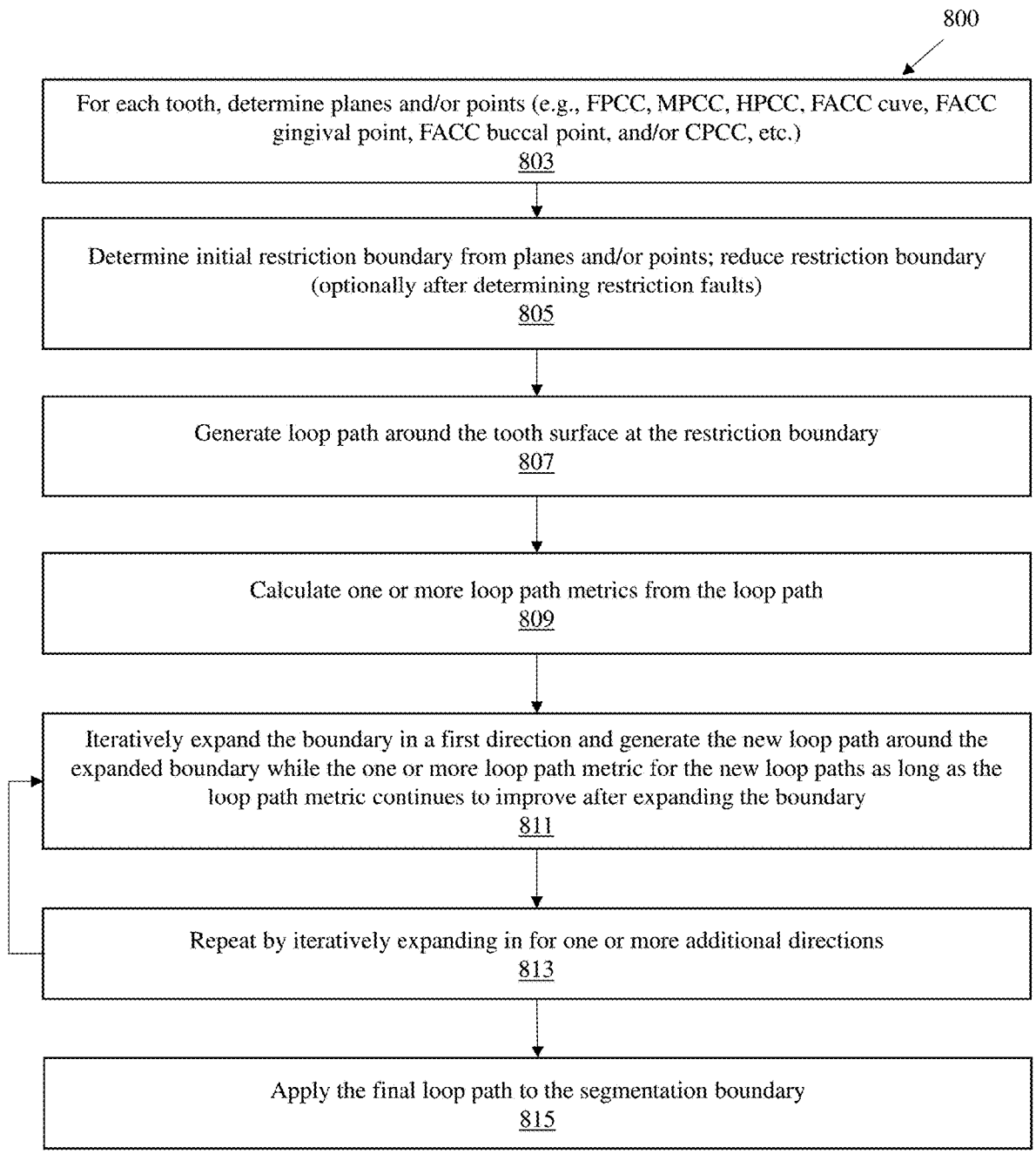
FIG. 8 illustrates one method 800 of performing segmentation backtracking as described herein

FIG. 8 illustrates one method 800 of performing segmentation backtracking as described herein. For example, in FIG. 8, for each tooth or putative tooth of a digital model of a patient's teeth, segmentation backtracking may include determining the planes, lines and/or points that may be used to form the boundaries (restriction boundaries) 803. For example, the method may include determining planes and/or points (e.g., FPCC, MPCC, HPCC, FACC curve, FACC gingival point, FACC buccal point, and/or CPCC, etc.) for each tooth or putative tooth. Segmentation backtracking may be done separately for each putative tooth either sequentially or in parallel.

The planes, lines and points may then be used to determine initial restriction boundaries 805, and (as the same step or a separate step) the method may include reducing the one or more restriction boundaries. This reduction may be optionally done after determining that there are restriction faults in which the resulting loop path extends off of the surface of the putative tooth (see, e.g., FIGS. 7A-7B, above). Alternatively the segmentation backtracking may be performed in every case.

Once the segmentation boundaries have been adjusted, the loop path around the tooth surface may be estimated using these segmentation boundaries 807. Sequentially or concurrently one or more metrics may be calculated for this loop path 809. Thereafter, the boundary may be expanded in one direction (or in some variations, in more than one direction) by a small amount, e.g., an increment. The increment may be determined or set by the user and typically is a fraction of the amount that the restriction boundary was reduced initially (e.g., 0.01%, 0.1%, 1%, 2%, 5%, 10%, 15%, 20%, 25%, etc.). The increment may be dynamically adjusted.

Figure 9:
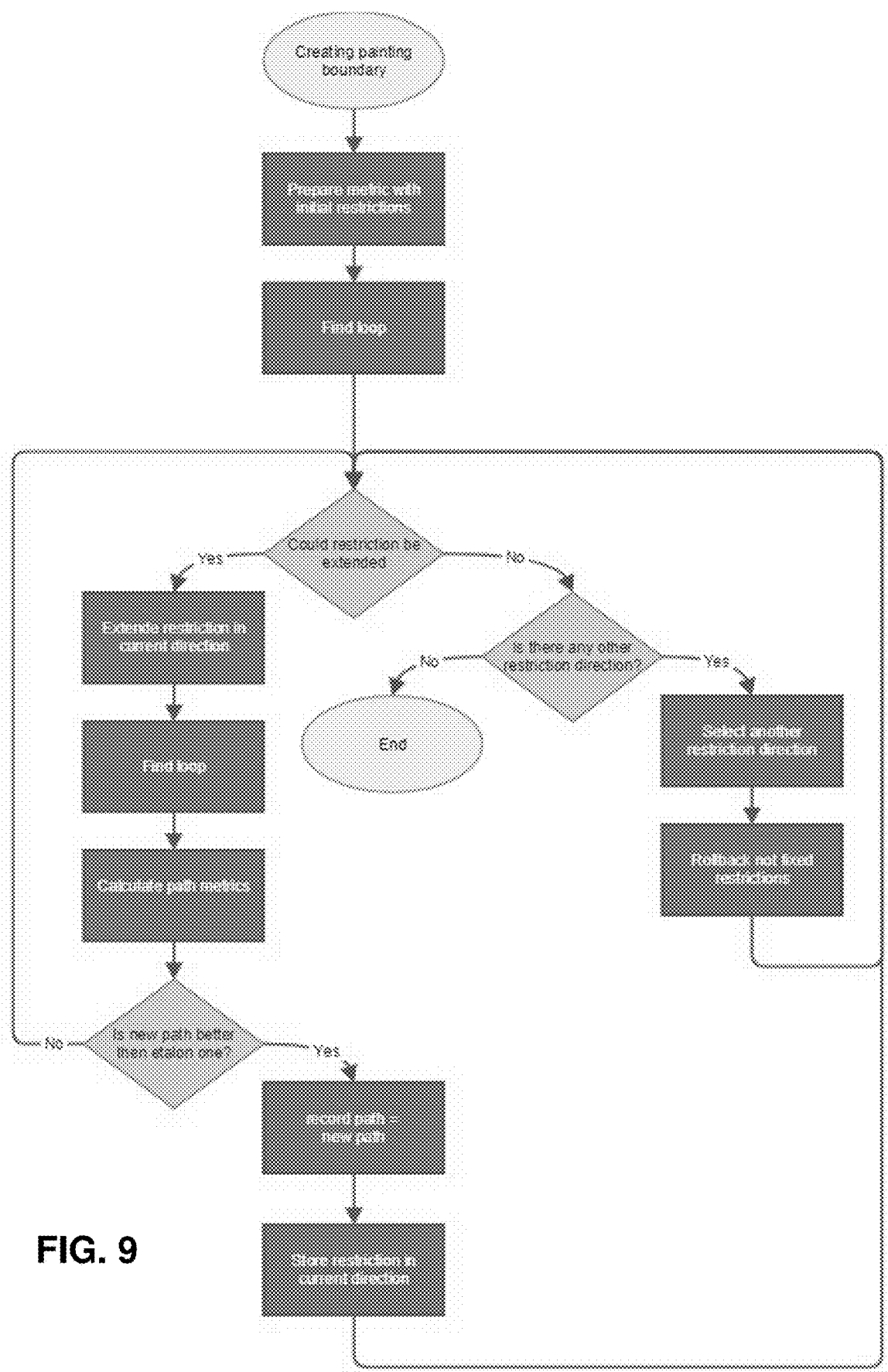
FIG. 9 shows another example of a flow diagram for the method of segmentation backtracking.

After each increase in the restriction boundary a new loop path may be generated and a metric calculated. This metric may be compared to the prior metric or a standard (set) value, and, the process repeated as long as the metric continues to improve 811. Once the metric starts to decline, the prior optimal value (the prior value of the restriction boundary) may then be set and this process may be repeated by iteratively changing the restriction boundary in another direction, estimating a loop path, and loop path metric. Additional directions may be optimized in this way until all or sufficient directions have been addressed 813. The resulting 'final' loop path may then be applied to the segmentation boundary 815, for example as the tooth-gingiva segmentation boundary. FIG. 9 is another example of a flow diagram for the method of segmentation backtracking described above.

Figure 10:
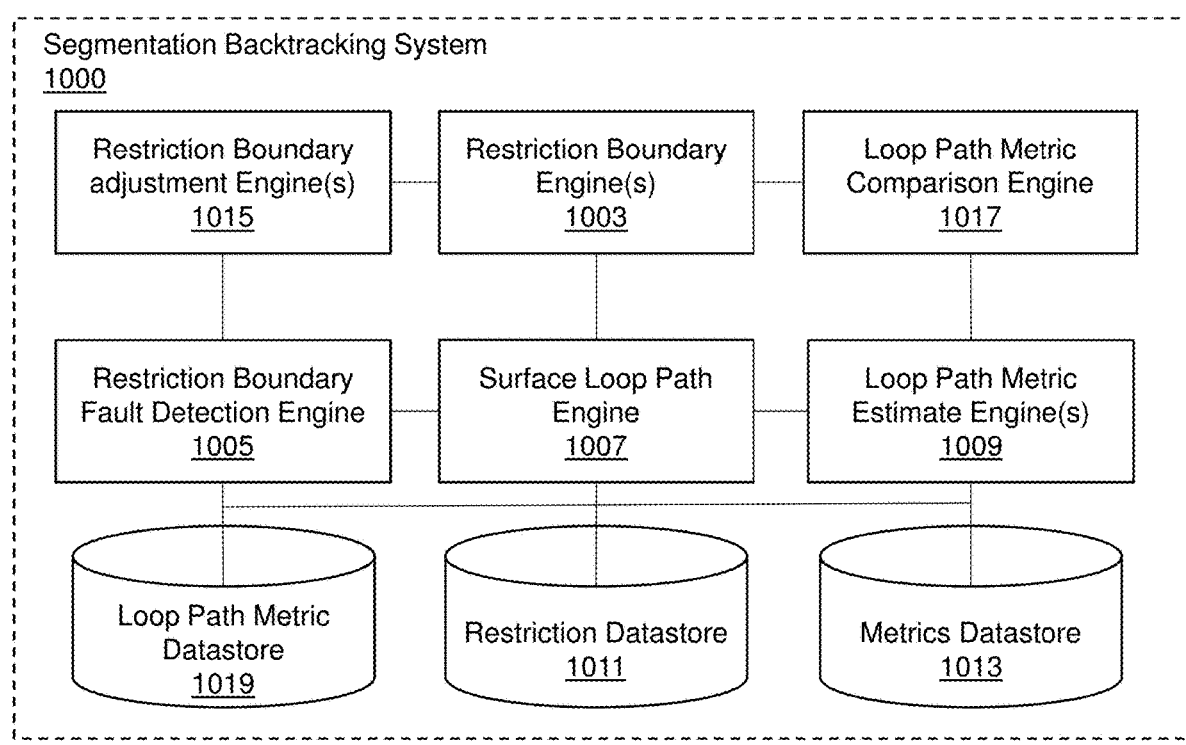
FIG. 10 is an example of a diagram showing an example of a segmentation backtracking system.

FIG. 10 is a diagram showing an example of a segmentation backtracking system 1000. The modules of the segmentation backtracking system 1000 may include one or more engines and datastores. A computer system can be implemented as an engine, as part of an engine or through multiple engines. As used herein, an engine includes one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used herein, datastores are intended to include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described herein.

Datastores can include data structures. As used herein, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described herein, can be cloud-based datastores. A cloud-based datastore is a datastore that is compatible with cloud-based computing systems and engines.

The segmentation backtracking system 1000 may include (or be partly integrated into) a computer-readable medium. As shown in FIG. 10, the segmentation backtracking system 1000 may include a restriction boundary engine 1003 that may, e.g., determine the restriction boundaries for one or each tooth (or a subset of teeth) from a digital model of a patients teeth, including from a digital scan. The restriction boundary engine 1003 may also determine planes and/or points (e.g., FPCC, MPCC, HPCC, FACC curve, FACC gingival point, FACC buccal point, and/or CPCC, etc.). The segmentation backtracking system may also optionally include a restriction boundary fault detection engine 1005 that may determine if there is a restriction fault in the existing restriction boundaries, as described above. A surface loop path engine 1007 may use a restriction boundary (or an adjusted restriction boundary, e.g., from a restriction boundary adjustment engine 1015) to calculate a surface loop path using the digital tooth model and the restriction boundary. A loop path metric estimation engine 1009 may apply one or more loop path metrics (which may be provide and/or accessed from a loop path metric datastore 1019) to estimate a metric associated with a loop path and restriction boundary; this information may be stored and/or accessed from a metrics datastore 1013. The system may also include a restriction boundary adjustment engine 1015 and a loop path metric comparison engine 1017 that may iteratively modify (e.g., increase) the restriction boundary calculate (via the surface loop path engine 1007) and estimate the loop path metric in one or more directions do determine a final restriction boundary value and corresponding surface loop path as described herein. This final loop path may be stored, transmitted and/or applied, e.g., to segment a digital model of the teeth.

The segmentation backtracking system may be automated and may implement one or more automated agents configured to apply the segmentation backtracking to one or more digital models of the patient's teeth.

Also described herein are processes for identifying the teeth, either from a segmented or unsegmented representation of the dental arch. Some implementations herein may solve technical problems related to optimizing and/or increasing the accuracy of digital dental scanning technologies. For example, in some variations the system or method may identify cusps corresponding to the patient's molars, and use the identified cusps to determine tooth numbering/identification. For example, the teeth may be automatically and accurately labeled using these methods and systems in a numbering standard (e.g., a universal number system or a modified universal numbering system) that further indicates the post-treatment tooth position score. For example, uppercase letters A through T may be used for primary teeth and the numbers 1-32 may be used for permanent teeth, as would be understood by those of skill in the dental/orthodontic art. Alternative standard dental numbering systems may be used (e.g., FDI World Dental Federation notation, Palmer notation, etc.).

Cusps Detection Algorithm

Following segmentation, including but not limited to any of the automatic segmentation methods described herein, it is useful to identify teeth, including labeling or numbering the teeth. For example, in one techniques referred to herein as cusp detection, teeth may be identified by detecting molar cusps, identify possible molar positions, and match these possible molar positions to tooth model positions.

It is often difficult to identify or detect all teeth from a digital scan. Even when teeth are accurately scanned at high resolution, teeth with otherwise well-defined shapes may be difficult to identify because of inclination, angulation, shift from teeth arch, etc. By detecting characteristics of molar cusps from a digital scan of a patient's dentition (e.g., a jaw scan) the adjacent teeth may subsequently be identified.

In general, molar cusp detection may identify cusps base on the convex areas with some geometry characteristics. In some variations, molar cusps may be detected and premolars (adjunct to them) may be detected. Cusp detection may use a maximum radius of surface to identify cusps and may use identified cusps to match or determine correspondence to molar shape based on cusp arrangement. Once a molar is identified, e.g., by the arrangement of cusps and/or one or more of: geometric, position and/or tooth-matching criterion, adjacent molars may be identified, as may adjacent pre-molars using similar techniques. By identifying all or some of the molars using molar cusp detection, adjacent teeth may be more readily identified, even when not in an expected order.

This technique was tested against a database of scanned teeth, and showed an increase in detection of all teeth of about 4% without significantly increasing processing time. In some variations, molar cusp detection may be combined with segmentation to improve the segmentation accuracy and/or speed. Further, molar cusp detection used to identify teeth had a very small false positive rate, which may be further reduced or eliminated by adding additional geometric, position or tooth-matching criterion.

For example tooth cusps may be identified, e.g., based on local maximum having adjacent curvature consistent with molar cusps, and the arrangement or pattern of adjacent cusps may be used to identify molars. Although this technique is particularly useful for determining molars, in some variations it may be used to identify one or more of: incisors, canine, premolars. Thus, characteristic maxima features, cusps, ridges, etc., may be used to identify tooth type, which may significantly improve the identification of ectopic teeth. Thus, molar tooth detection may be used to identify teeth even when they are present out of the dental arch.

In general the use method of cusp detection described herein may be configured to be adjustable to detect cusps and ridges, for example, by adjusting the radius of the 'cusp' region (e.g., maximum surrounded by different radius to detect cusps and ridges.

In some variations, the molar cusp detection may also find one or more groove areas in a scan surface and use the one or more groove areas with the detected cusps to predict molar position. The use of additional features, and particularly adjacent local minima surface, such as grooves, may significantly improve cases where fewer than 3 cusps are detected (e.g., where only 1 or 2 cusps can be detected). In some variations, the molar cusp detection may be implemented to detect molars even where only two cusps are identified, which may be sufficient to match teeth in a position to detect, e.g., ectopic tooth, even when the tooth rotation is unknown.

Figure 11:
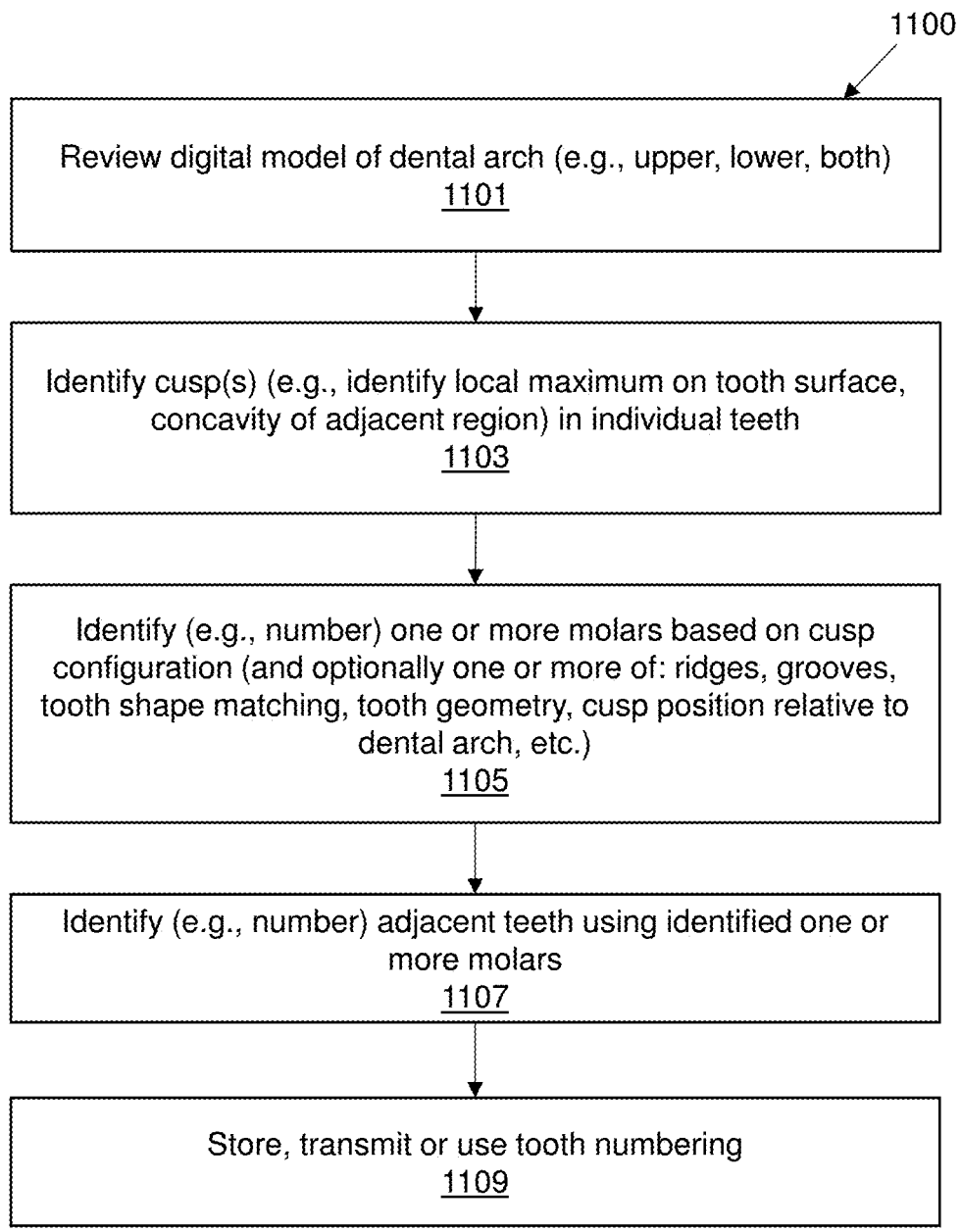
FIG. 11 shows an example of a method of molar cusp detection as described.

FIG. 11 illustrates one example of a method of molar cusp detection as described herein. In FIG. 11, the method may include reviewing the digital model of dental arch (e.g., upper jaw, lower jaw, both jaws) 1101, and may further include identifying one or more cusp(s) (e.g., identify local maximum on tooth surface, concavity of adjacent region) (e.g., two, three, etc.) in individual teeth 1103. The identified cusps, which may be associated with putative teeth (e.g., segmented teeth) may then be identified as part of one or more molars based on cusp configuration (and optionally one or more of: ridges, grooves, tooth shape matching, tooth geometry, cusp position relative to dental arch, etc.) 1105. The molars and/or the other teeth may then be identified, including identifying the adjacent teeth using identified one or more molars. The identified teeth may be numbered, e.g., by number, such as a universal tooth numbering system 1007. The tooth identity may then be stored, transmitted and/or used 1109.

Method And Apparatus for Testing Teeth Segmentation

Also described herein are methods and apparatuses for determining how robustly a digital representation of a patient's dental arch has been segmented into component parts such as teeth gingiva, etc. As described above, segmentation may generally include three dimensional (3D) scanning (e.g., surface scanning of a patient's teeth) and teeth recognition (see, e.g., U.S. Pat. No. 6,409,504, herein incorporated by reference in its entirety). Optionally a method or workflow including segmentation may include using the resulting segmented model of the teeth for treatment planning and/or sending the case for review. Unfortunately, automatic teeth recognition (e.g., segmentation) may contain errors. Thus, it would be desirable to test a segmented digital model to identify problems with the segmentation and/or to evaluate the overall accuracy of the segmentation of the digital model. This information may be used to revise or adjust the segmentation and/or to reduce or prevent problems that may arise from less accurate segmentation. Thus, the methods and apparatuses for checking segmentation described herein may be useful for filtering poorly segmented cases and routing them for further processing, including manual processing in some cases.

As discussed above, segmentation is a process of recognizing teeth on the scan and creating separate object for each tooth. Automatic segmentation may result in inaccuracites that may be reprocessed and/or manually adjusted to proceed to creation of treatment. A segmentation testing system may automatically or semi-automatically review segmentation of one or more digital representations of a patient's teeth, and may determine (e.g., rank, rate, etc.) the quality of the segmentation. In some variations, the system may filter out poorly segmented digital representations. In some variations the system may indicate a pass/fail ranking; alternatively or additionally, the systems described herein may provide a score for the segmentation. Alternatively or additionally, the system may be part of another system (e.g., may be a subsytem) that may trigger automatic or semi-automatic re-processing (re-segmentation) of the case.

In order to distinguish good segmentation from poor segmentation, a testing system as described herein may include a filtering system having one or more filters. Each filter may represent one or more separate segmentation parameter. In some variations, if a check for any one of these segmentation parameters fails, the case may be considered for re-segmentation, potentially including manual adjustment; in some variations, cases that pass may automatically proceed to treatment creation.

In some cases the filters may be machine learning filters. For example, a filter agent may be trained on one or more parameters to identify pass/fail (or scoring) criterion. In some variations a filter or filter agent may be created by training the filtering agent against both positive groups (e.g., manually processed scans of a case or cases for which segmentation is a high quality) and negative groups (e.g., processed scans of a case or cases, in some variations the same case or cases, that are poorly segmented). Cases may be compared by various test metrics such as, but not limited to: shape of resulting tooth crown, numbering of teeth, spaces between teeth, etc. One or more filters that determine and/or identify deviations from acceptable parameters for one or more of these metrics may be created and used. As the number of test metrics by which a case can be compared may be quite large, the number of filters can be constantly updated, so that the system may learn to distinguish between good and bad cases more precisely.

In some variations, rather than a machine-learning agent, one or more comparison filters may be provided, in which quality metrics identifying well-segmented vs. poorly segmented data files may be described. Manual filters may include calculation of one or more parameter quality estimates for a segmentation of a digital model of a patient's dentition.

In any of the methods and apparatuses described herein, a report may be generated. Alternatively a score, with or without a report, may be generated.

Figure 12:
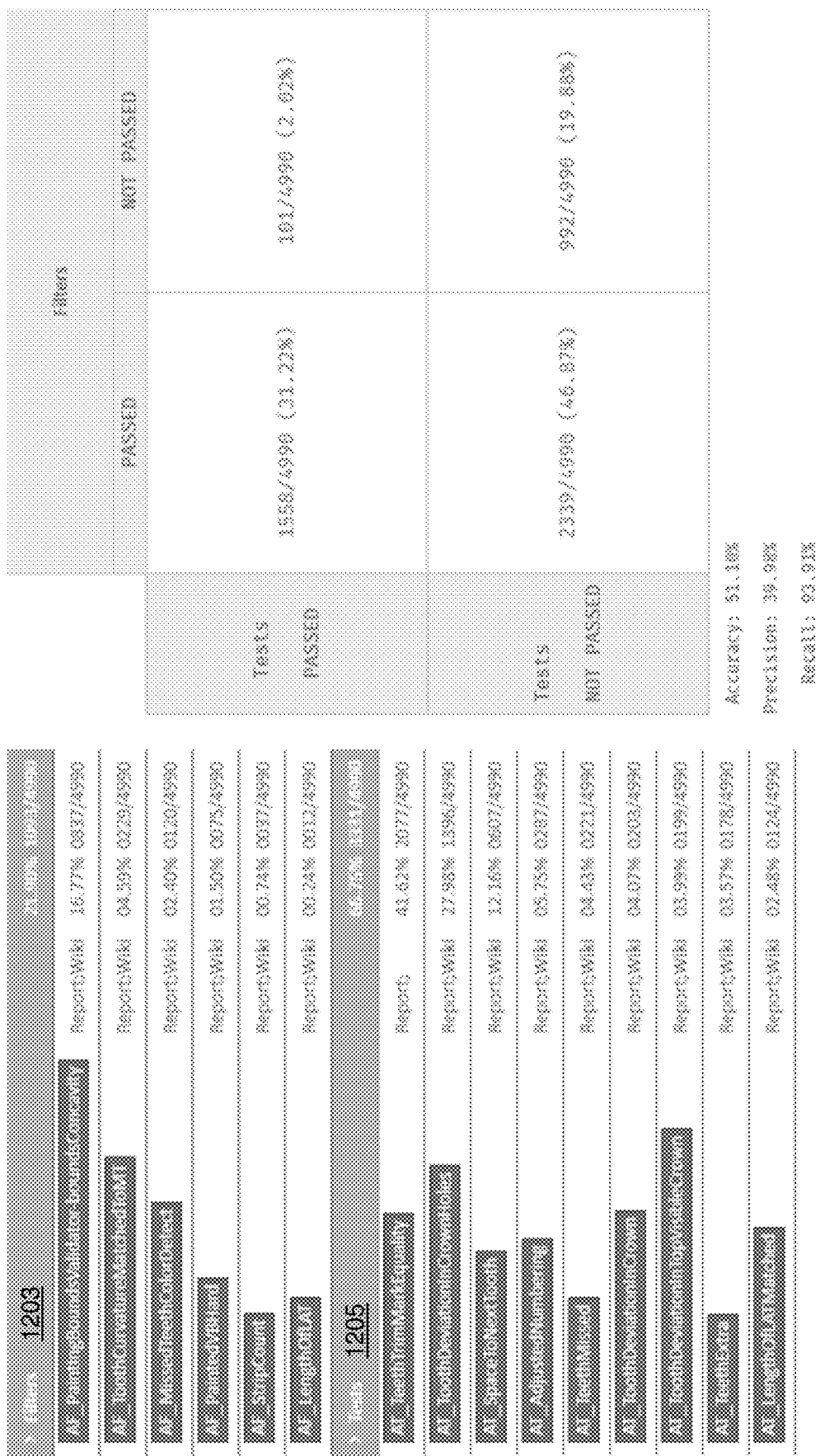
FIG. 12 is an example of a segmentation test report as described herein.

For example, FIG. 12 illustrates one example of a segmentation test report. In this example, the test report includes an indication of the results of six different filters 1203 and nine different tests 1205. The report shown in FIG. 12 is an aggregation of the quality of segmentation for a collection of segmented digital models; in practice a report may be specific to a particular digital model that has been segmented.

In the example shown in FIG. 12, in order to determine that the trained filters are working properly, the results of filtering were compared with a variety of different test metrics results. In the best case, filters should not fail cases that have passed the test metrics, and vice versa. In contrast, difference between the trained filter results and the tests may suggest that either the test metrics or the filters may be adjusted to achieve a proper result. The report shown in FIG. 12 is a dedicated report.

In general, the results of a testing system such as those described herein may be useful for determine which cases can skip manual review and adjustments and proceed directly to creation of a treatment (e.g., to generate a treatment plan), which may save a lot of time on overall processing. The systems described herein may be flexible and can be adjusted and/or updated in order to increase precision of case quality detection.

A possible workflow for this testing segmentation may include: detecting (by applying filters, such as trained filters and/or tests) the quality of an automatically segmented digital model of a patient's dentition. Cases that pass the testing may proceed to treatment creation and cases that fail (having bad segmentation) may be re-segmented using an alternatively method and/or following adjustment of the segmentation parameters and/or the digital description.

Figure 13:
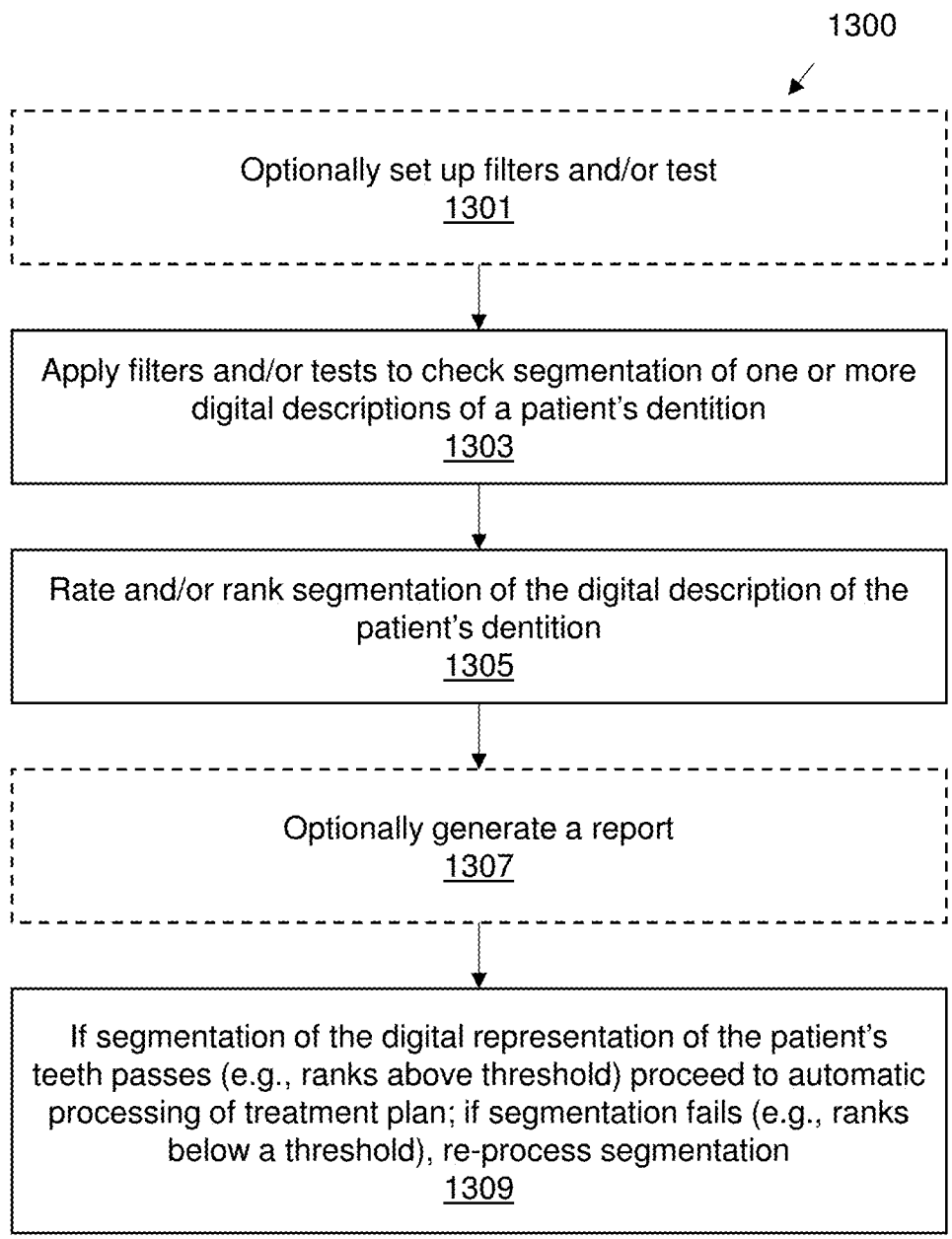
FIG. 13 illustrates one example of a method for automatically testing the quality of segmentation.

For example, FIG. 13 illustrates one example of a method for testing the quality of segmentation (automatically). In FIG. 13 an optional initial step may include setting up the filters and/or tests applied 1301. For example, as mentioned above, in some variations the filters may be filter agents that are trained to recognize and/or rate or rank segmentation, including one or more specific segmentation parameters. Alternatively or additionally the methods and apparatuses for testing segmentation may be adjusted by modifying one or more parameters or parameter conditions. In some variations, as mentioned briefly above, this may include feedback from the testing itself, which may indicate filters or filter agents and/or tests that are more or less stringent than necessary.

In FIG. 13, the method may include applying one or more filters and/or tests to check the segmentation of one or more digital descriptions of a patient's dentition 1303. In any of these methods the filters may check one or more of: tooth shape, tooth count, tooth position, surface boundaries, missing teeth, extra teeth, tooth crown shape, tooth crown orientation, space between teeth, tooth surface curvature, gingival border, trimmed teeth, tooth numbering, visible top of crown, holes in segmentation, etc.

The output of the one or more filters or tests may be combined into a score or collection of scores 1305. In some variations a final score (e.g., rank, rating, grade, etc.) may be calculated. The scores, including the final scores, may be qualitative (e.g., pass/fail) or quantitative (numeric, etc.), such as a ranking from 0-100. The final score may be a sum, average, weighted sum, weighted average, etc. of all or some of the component scores. Optionally, the method or system may generate a report 1307 including some or all of the scores.

In general, the output of a system for testing the segmentation of a digital representation of a patient's teeth (e.g., a digital model) may be used to automatically process (or not process) the digital model to form a treatment plan for an orthodontic treatment. For example, if segmentation of the digital representation of the patient's teeth passes (e.g., ranks above a threshold) proceed to automatic processing of treatment plan; if segmentation of the digital description fails (e.g., ranks below a threshold), the digital representation of the patient's teeth may be modified and/or segmented again, including, in some variations, manually segmented 1309. Alternatively or additionally, as described above in relation to FIG. 12, the results of the testing can be used for improving of automatic segmentation itself.

Quality Assessment Based on Color

In addition, or alternative to the assessment of segmentation quality described above, in some variations the assessment of quality may be based at least in part on the use of color information received by tooth scan. Although color may vary between patient dental scans, making direct comparison difficult, color information may be stable (or may change in a continuous manner) within a single scanning session, and this color information may be used to aid in segmentation and/or to assess the quality of a segmentation. For example, described herein are both method of improving segmentation and/or tooth identification using color as well as methods and apparatuses for assessing the quality of segmentation. For example, the color may be used for clusterization of teeth and gingiva based on color.

Figure 14A:
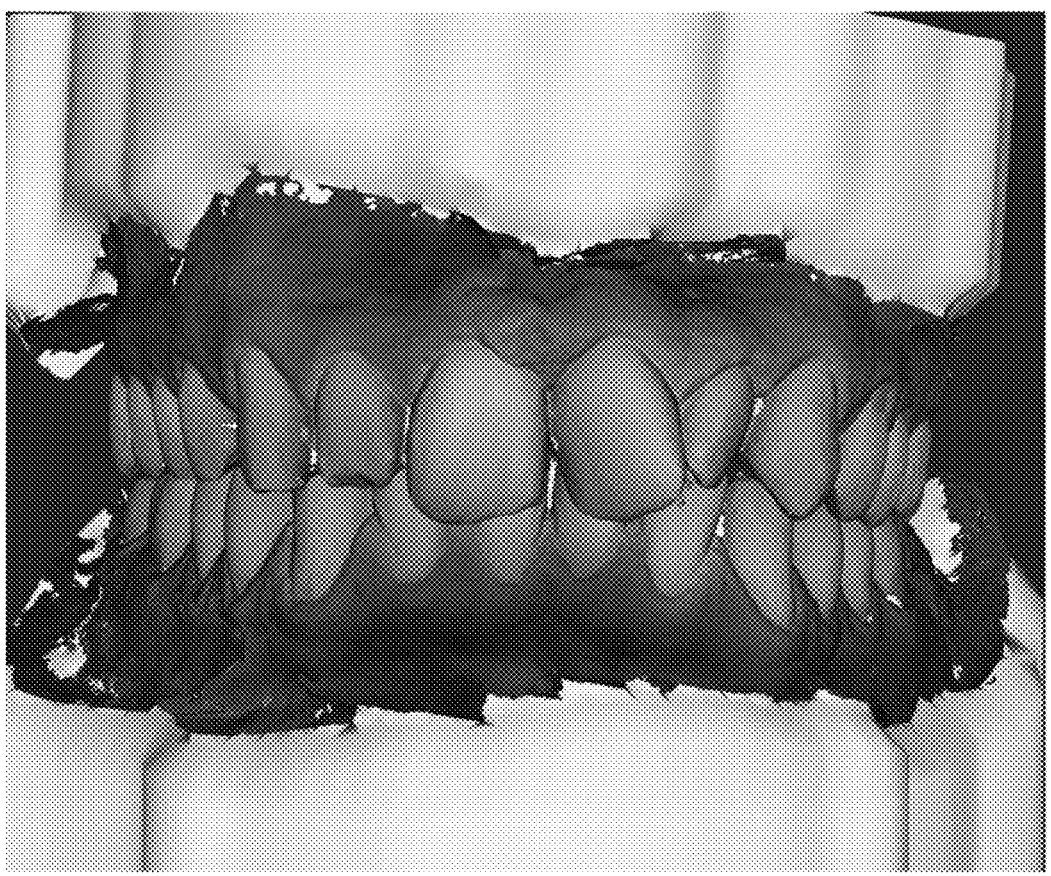
FIG. 14A shows an example of a color digital scan of a patient's upper and lower jaw.
Figure 14B:
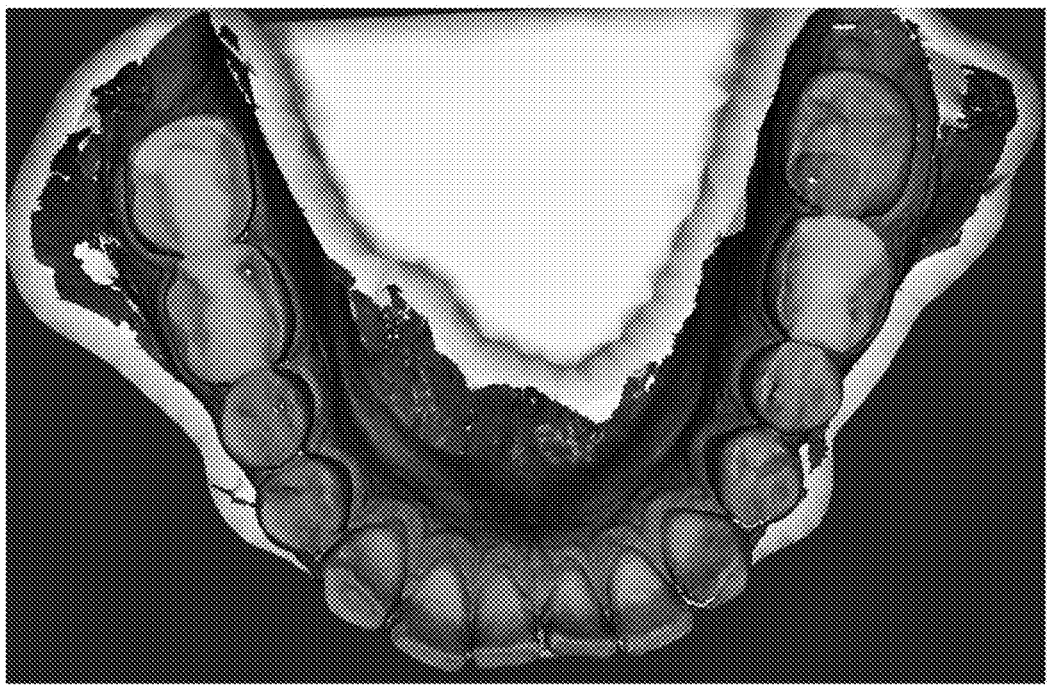
FIG. 14B shows an example of the color-scanned lower jaw.

FIGS. 14A and 14B show examples of a digital surface model of a patients teeth and gingiva, taken with an intraoral scanner, e.g., the iTero™ intraoral digital scanner manufactured by Align Technology, Inc. This scan may be performed in color, and the digitized color information included as part of the digital file, as shown. FIG. 14A shows an example of a digital scan of a patient's dental arch (showing the upper and lower jaw), including color information. FIG. 14B shows an example of the color-scanned lower jaw. In this example, the scans illustrate teeth that may not be detected/extra teeth. For example, segmentation in which cusps (e.g., molar cusp detection) are detected may not readily identify the molars 1405 in which the cusps have been worn flat. However in these situations the additional and/or alternative use of color to segment or assist in segmentation may be useful.

Figure 15:
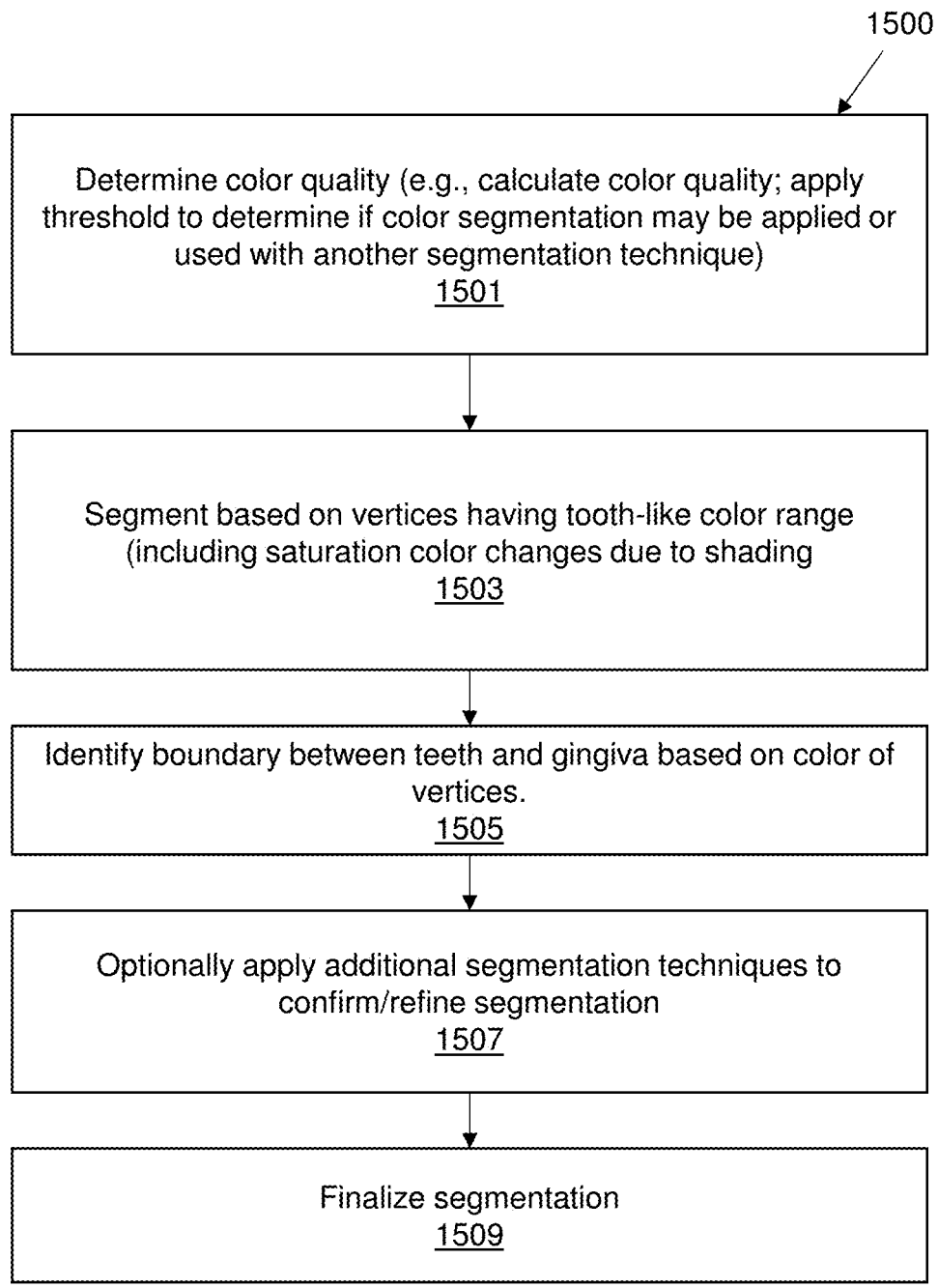
FIG. 15 illustrates one example of a method of segmenting a digital model of a patient's teeth that include color information from the scan.

FIG. 15 illustrate one method of segmenting a digital model of a patient's teeth 1500 that include color information from the scan. Color information from a digital scan may be used for segmentation after first confirming that the quality of the color data in the scan is sufficient 1501. This may be determined as described below in reference to FIGS. 17A-17I. Some color wavelengths may be particularly helpful, such as color within the green and blue wavelengths, while red wavelengths are less useful. Thus, changes in color from green and blue wavelengths may be used to distinguish boundary regions between, e.g., the teeth and the gingiva 1503. In some variations, boundaries for segmentation may be determined or refined using the color data.

In general, regions of the surface that are "teeth colored" (within a range of color values particularly green and blue color values) are initially marked as teeth. The colors associated with the teeth in the scan may be preset or may be determined by combining with other segmentation techniques, including shape identification (e.g., molar crown identification, as described above), or any other segmentation technique, and taking the color (or average color values) from regions identified by these additional segmentation techniques as teeth. The use of color for segmentation may be combined with and/or incorporated into any appropriate segmentation technique.

Segmentation by color as shown in FIG. 15 may include identifying tooth surface regions by identifying regions (e.g., vertices) in the digital surface that include cluster of tooth-like coloration 1503. The boundaries of the teeth may be defined based, in part, on regions in which color values change, and in particular, where the blue and/or green values change in a manner that is not consistent with changes due to intensity (e.g., shadows, lighting, etc.). This may be seen as a discontinuity in the color values. For example, the boundary between the teeth and the gingiva may be identified base on the differences in the color values of the regions 1505.

As mentioned above, any of these methods may optionally include additional techniques for segmenting, including at least those described herein 1507, which may further refine the segmentation of the teeth. This process may be iterative, in which boundaries used to segment the teeth may be adjusted by the use of the color segmentation described herein and then the boundary-based segmentation may be re-run until the process is finalized 1509.

Figure 16:
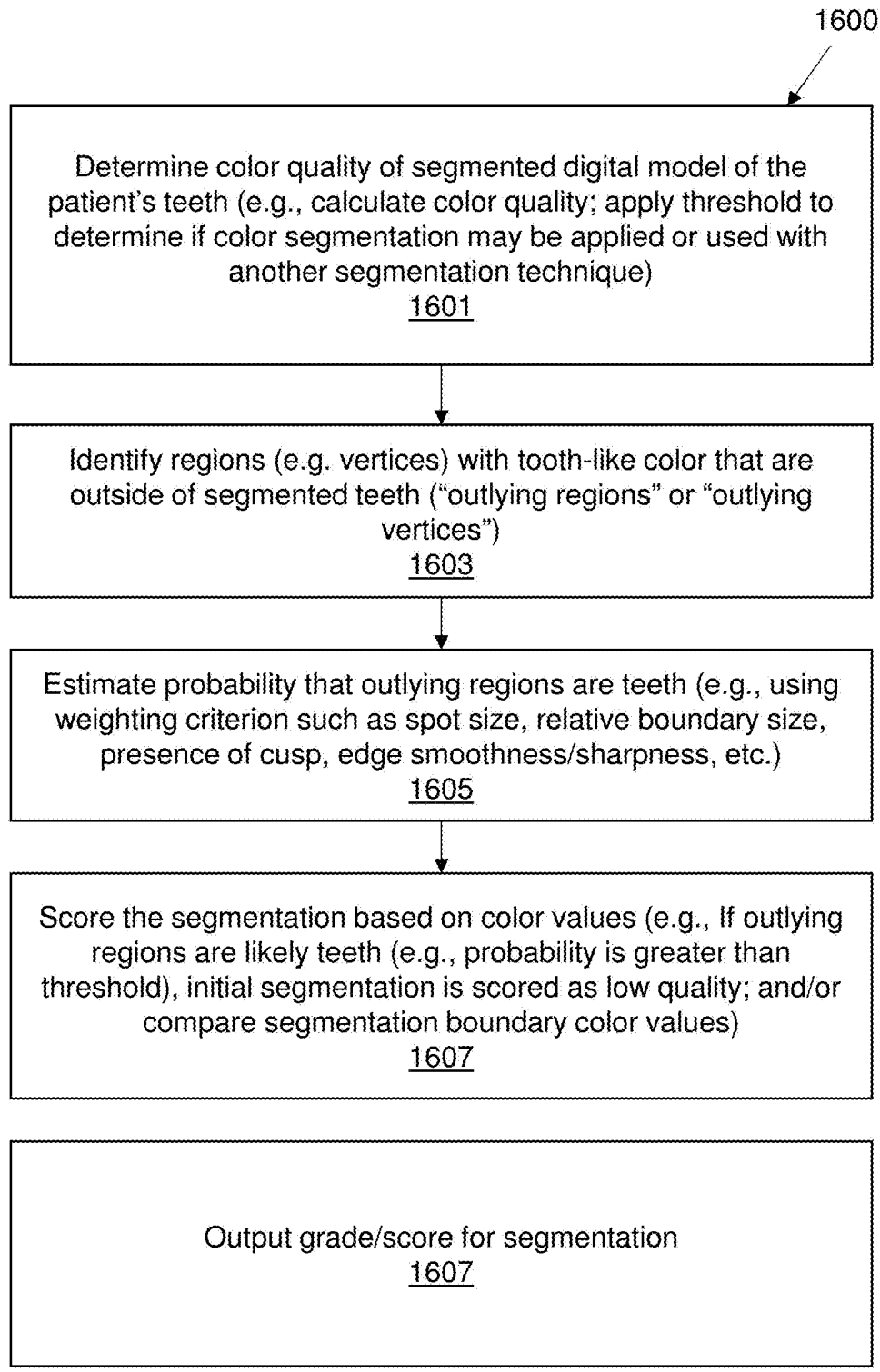
FIG. 16 illustrates one example of a method of assessing a segmented dental model of a patient's teeth that uses color information.

Also described herein is the use of color information to grade, score or otherwise assess the quality of segmentation of a digital model of a patient's teeth. For example, FIG. 16 illustrates one method of assessing a segmented dental model of a patient's teeth that uses color information 1600. Initially a system using this method may calculate the color quality of the segmented digital model 1601. The segmented digital model, which includes color information, may be received or accessed, and the color values of the surface(s) examined. Digital models (e.g., digital representations of the patient's teeth) in which the color quality is too low may not be used for unsegmented teeth detection. Example techniques for assessing color quality are described in greater detail below. For example if the range of color values is low (e.g., below a threshold) and/or the distribution of color values is too narrow, etc. If the color quality is sufficient, then the method may continue. This step may be the same as the use of color for segmentation described above.

In the variations described herein, the digital model of the patient's tooth may be expressed as a surface including a plurality of vertices; each vertex may include the color value associated with that portion of the scan. In general, the digital model may be constructed from a scan (e.g., a plurality of 2D scan images, particularly color images) in any appropriate manner, not limited to mesh or mesh-like digital models. Any of the methods described herein may include forming the digital surface (e.g., 3D) model of the teeth from the scan data, and/or may include accessing the surface model.

Once the color quality of the segmented digital model of the patient's teeth has been verified as adequate, regions with tooth-like color may be identified 1603, and in particular, regions (e.g., vertices) of tooth-like color that are not segmented into teeth (or portions defined as teeth in the segmented model) may be identified. In some variations this method or a method similar to it, may be used to assist in identifying teeth from segmented regions of a digital model. Regions with tooth-like coloring (color values) that are outside of the segmented teeth identified in the model may be referred to as outlying regions (or outlining clusters of regions). Any outlying clusters may then be analyzed to determine if they are outlying teeth 1605, which may be determined, for example, by comparing to other tooth models. This information, as well as other color information, may be used to score the quality of the segmentation 1607. For example, the methods and apparatuses may estimate the probability of such tooth-colored outlaying regions being actual teeth using one or more criteria including (but not limited to): the size of the cluster, the relative boundary size of the cluster, the shape of the cluster, the presence or absence of a cusp on the cluster, the presence of sharp edges (which may be typical for moving tissue), etc. If the weight of these criterion indicate that the regions corresponding to a tooth, the case segmentation may be marked as low quality, because of undetected tooth. Alternatively or additionally, the segmentation boundaries may be examined for color. For example if the color values in the regions of the boundary, and particularly the blue and green range color values, are similar (within some defined range, e.g., within 1%, 2%, 5%, 7.5%, 10%, 15%, 20%, 25%, etc.) of the color range in a region on both side of the boundary (e.g., within a few vertices), then the boundary, and therefore the segmentation, may be scored as inaccurate; in some variations, the closer the color values are on either side of the segmentation boundary, the lower the quality score may be.

As mentioned, in any of the variations described herein, color assessment may be performed on the digital model before using the color values for segmentation, identification of segments and/or grading the quality of segmentation, as described above. Color quality calculation is important because color distribution may vary significantly across different cases. Color values may be affected by various factors, such as illumination during scanning process, scan wand hardware properties and scanner software version. In general, color quality is a metric that describes how well the regions (e.g., vertices) of a scan can be divided into two groups (e.g., clusters), such as gingiva-like colored regions and teeth-like colored regions.

Figure 17A:
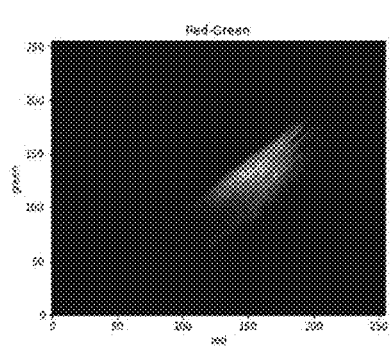
FIGS. 17A-17I show examples of color histograms from a segmented color digital scan of a patient's teeth showing the relative distribution of pairs of colors (e.g., red-green, red-blue, green-blue) for the patient's teeth, gingiva and entire jaw.
Figure 17B:
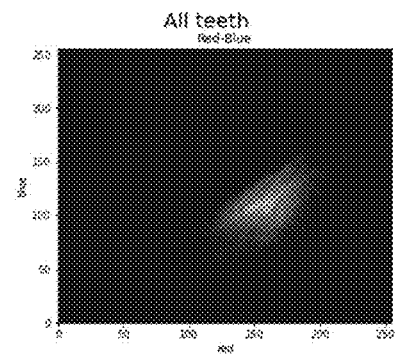
Figure 17C:
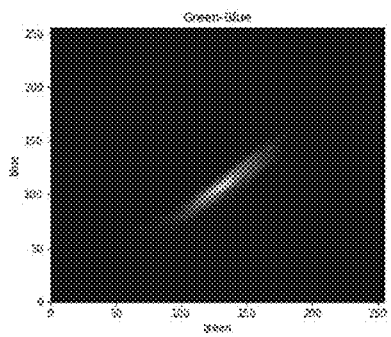
Figure 17D:
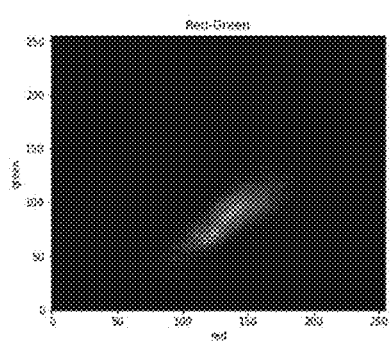
Figure 17E:
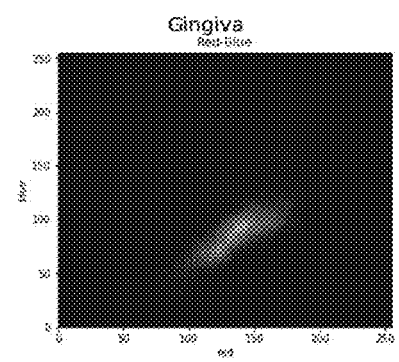
Figure 17F:
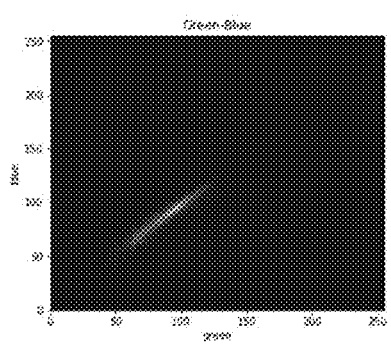
Figure 17G:
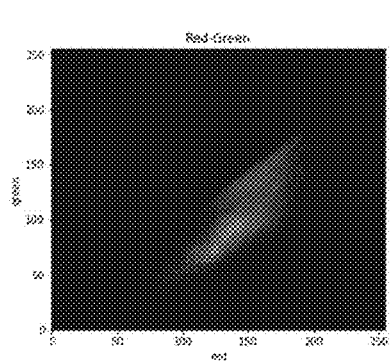
Figure 17H:
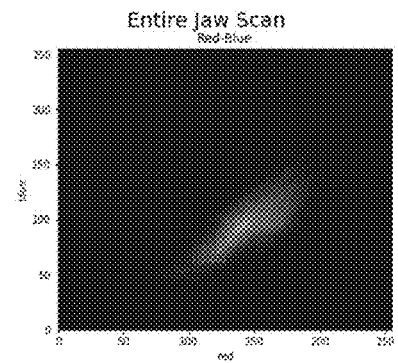
Figure 17I:
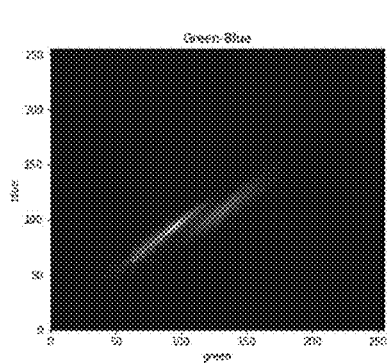
Figure 17J:
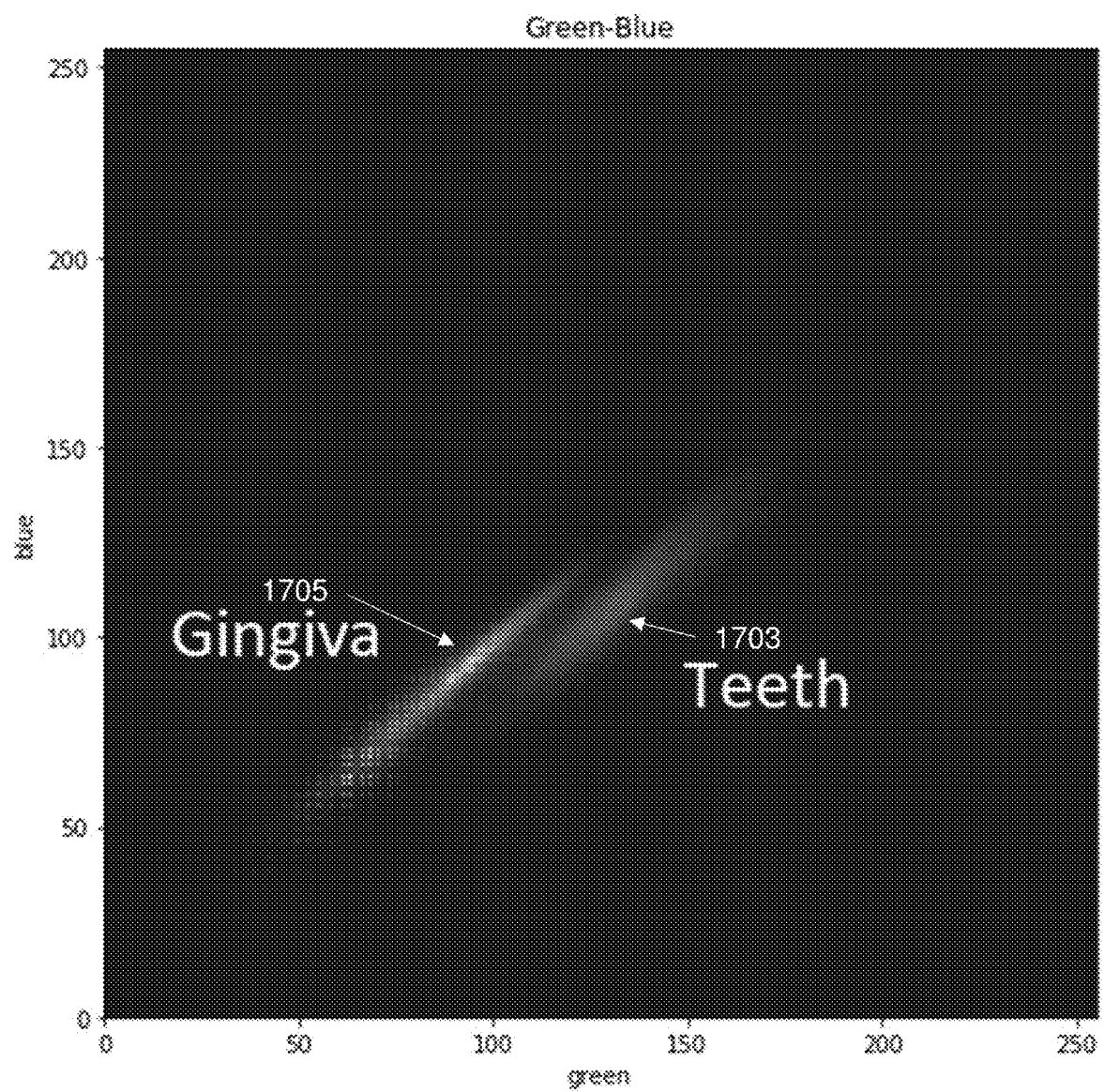
FIG. 17J is an enlarged view of the green-blue distribution histogram (from FIG. 17I) showing the separation between the gingiva and the teeth in these color ranges.

Useful features of color distributions may be identified by scatter plots. For example, FIGS. 17A-17I show scatter plots constructed from an example digital model of a patient's dentition; the digital model used is from existing segmentation data that was manually checked to be valid. FIG. 17J shows the green-blue color regions specifically. For example, FIGS. 17A-17C show the color plots for all regions identified as teeth in red-green (FIG. 17A), blue-red (FIG. 17B) and green-blue (FIG. 17C). In this example, the scatter distribution of green-blue is most tightly correlated. FIGS. 17D-17F show similar scatter plots for regions identified as gingiva (e.g., FIG. 17D shows red-green, FIG. 17E shows red-blue and FIG. 17F show green-blue). Finally, FIGS. 17G-17I show the result of the entire jaw scan. FIG. 17I is shown in an enlarged view in FIG. 17J, showing the separation in the scatter distribution for the green-blue color range between teeth 1803 and gingiva 1805. Thus, as is clearly seen on green-blue plots, the gingiva color and teeth color forms two distinguishable clusters in these wavelengths, indicating a significantly different characteristic distribution of coloring in these regions. The red color component usually has an irregular shape and typically does not differ as much between teeth and gingiva. Therefore, it may be beneficial to use one both of the green and blue color components for color quality assessment and segmentation.

Since green-blue color distribution may be shaped similarly to an ellipse, in some variations, the chosen approach may be to use a Gaussian mixture model (GMM) using Expectation-Maximization (EM) to analyze the digital model. A useful property of GMM is that instead of hard labeling, it assigns cluster membership coefficients for each point. These coefficients may then be used to calculate partition coefficient (similar to fuzzy partition coefficient from fuzzy k-means algorithm):

$$V_{PC} = \frac{1}{N} \sum_{i=1}^{c} \sum_{j=1}^{N} (u_{ij})^2$$

Where: $V_{pc}$ refer to the partition coefficient, N is the number of points, C is the number of clusters (in our case, 2), and $U_{ij}$ is the probability of point j belonging to cluster i. Typically $V_{pc}$ lies in range [0, 1]. Higher values may indicate better clustering, which means higher color quality.

Figure 18A:
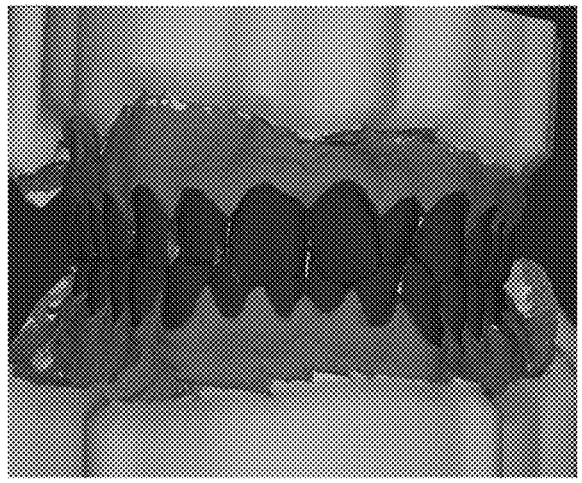
FIG. 18A shows an example of a digital scan of a patient's teeth in which there is a high degree of color distribution in the scan (including between teeth and gingiva).
Figure 18B:
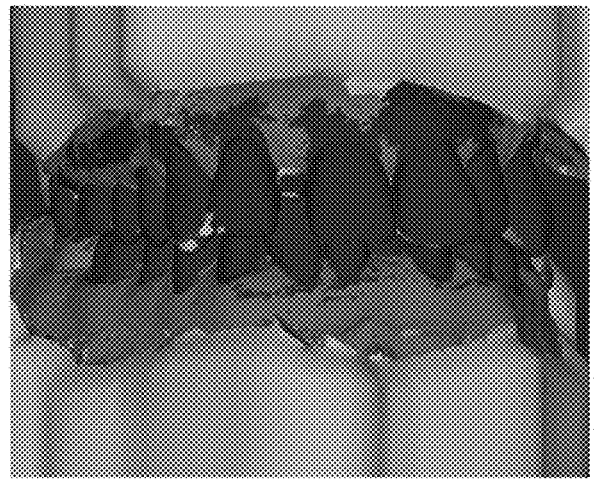
FIG. 18B shows an example of a digital scan of a patient's teeth in which there is a low degree of color distribution in the scan.

For example, cases with very high color quality (e.g., $V_{pc}$=0.98) and low color quality ($V_{pc}$=0.84) are shown in FIGS. 18A and 18B, respectively. In FIG. 18A there is a significant distinction between the tooth and the gingival color, as shown, particularly as compared to FIG. 18B. Indeed, in some instances, cases with very high color quality thus be segmented using color only. An estimate of the color distribution (as described above in reference to FIG. 15) may be used as a threshold indicator that segmentation by color may be used.

In general, as described above, color values may be used to assess segmentation of a digital model of a patient's teeth. For example, the approach descried above in reference to FIG. 16 may be used to identify unsegmented teeth and/or to assess the sharpness of the boundary between teeth and gingiva.

Figure 19:
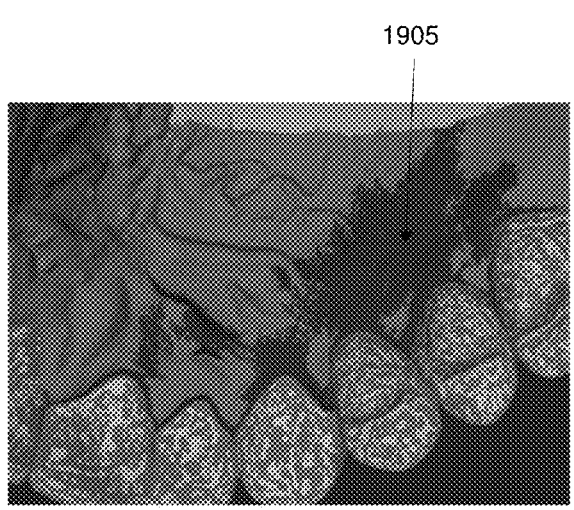
FIG. 19 is an example of a digital scan in which clusters with coloration similar to the teeth are found outside of the segmented tooth range; these clusters have poorly-defined boundaries.
Figure 20:
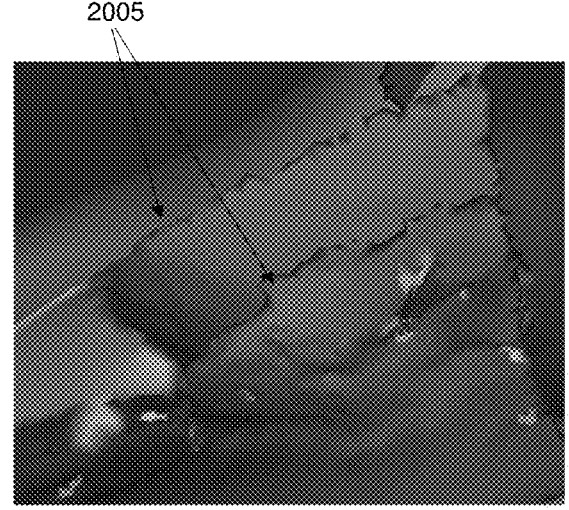
FIG. 20 is an example of a cluster of vertices having a color value similar to a tooth but having sharp edges, likely resulting from a motion artifact during the scan.

For example, when identifying outlying regions (outlying vertices or clusters) that are colored like teeth, but not marked after segmentation completion, the method or apparatus may verify that the outlying cluster is a tooth based on the size of the outlying cluster. This may be done quickly and computationally inexpensively, because a size check is typically fast and may filter out all small clusters. Furthermore, small clusters may tend to introduce more false positives, than true positives. In some cases, the clusters must have relatively compact boundary to be considered a missed tooth. This may filter out ill-defined clusters 1905, such as the example shown in FIG. 19. In some variations, the cluster of tooth-colored regions may be considered more likely to be a tooth when it contains at least 50% of any detected cusp regions. This may also assist in filtering out false positives, which may come from lightly-colored clusters on gingiva. Clusters may also be limited to those that do not contain too many sharp edges 2005, which may be more likely to be motion artifacts. See, e.g., FIG. 20. This may assist in filtering out false positives connected to moving tissue (which can be colored like a tooth), as shown. Combining some or all these conditions may result in a high confidence that the unsegmented teeth detection based on the identifying tooth-colored clusters is effective. As mentioned above, this may be used to score the segmentation and/or to modify or enhance segmentation. For example this approach may be used as part of a supplemental segmentation search for additional teeth.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A computer-implemented method comprising:
   determining, for a tooth of a digital model, a first restriction boundary for the tooth;
   generating a loop path around a surface of the digital model of the tooth based on the first restriction boundary;
   estimating a loop path metric from the loop path;
   adjusting the first restriction boundary by iteratively expanding the restriction boundary in a first direction and generating a new loop path based on the expanded restriction boundary until a second loop path metric that is estimated from the new loop path no longer improves, wherein the first restriction boundary is adjusted until the second loop path metric is larger than a loop path metric prior to expanding the restriction boundary;
   repeating the step of adjusting the first restriction boundary for one or more additional directions; and
   segmenting the digital model of the tooth based on a final adjusted first restriction boundary.

2. The computer-implemented method of claim 1, further comprising estimating the first restriction boundary for the tooth based on one or more of: a facial plane of the clinical crown (FPCC), a middle plane of the clinical crown (MPCC), a plane orthogonal to a Z-axis of the tooth (HPCC), a facial axis of the clinical crown (FACC) curve, an FACC gingival point, an FACC buccal point, and a central plane of the clinical crown (CPCC).

3. The computer-implemented method of claim 1, further comprising confirming that the restriction boundary is faulty.

4. The computer-implemented method of claim 1, wherein segmenting the digital model of the tooth based on a final adjusted first restriction boundary comprises segmenting the digital model of the tooth between the tooth and the gingiva.

5. The computer-implemented method of claim 1, wherein the loop path metric comprises a path curvature for the loop path or the new loop path.

6. The computer-implemented method of claim 1, wherein the loop path metric comprises a mean or variance of the path curvature for the loop path or the loop path metric.

7. The computer-implemented method of claim 1, wherein the loop path metric comprises a length of any convex edges of the loop path.

8. The computer-implemented method of claim 1, wherein the plurality of filters comprises one or more filters configured to check one or more of: segmented tooth shape, tooth count, segmented tooth position, segmented surface boundaries, missing teeth, extra teeth, segmented tooth crown shape, segmented tooth crown orientation, space between segmented teeth, segmented tooth surface curvature, segmented gingival border, trimmed teeth, tooth numbering, visible top of crown, and holes in segmentation.

9. A computer-implemented method comprising:
   applying a plurality of filters to check the segmentation of a segmented digital model of a patient's dentition;
   ranking the segmentation of the segmented digital model of the patient's dentition based on the results of the plurality of filters by averaging a numerical score from each of the filters of the plurality of filters; and
   automatically processing the segmented digital model of the patient's dentition if the segmentation of the segmented digital model of the patient's dentition is ranked meets a threshold rank.

10. The computer-implemented method of claim 9 wherein automatically processing comprises automatically processing the segmented digital model of the patient's dentition if the segmentation of the segmented digital model of the patient's dentition is ranked meets a threshold rank, otherwise re-processing the segmentation of the segmented digital model of the patient's dentition.

11. The computer-implemented method of claim 9, further comprising generating a report and presenting the report to a user or technician.

12. The computer-implemented method of claim 9, wherein at least some of the filters comprise machine learning filters.

13. The computer-implemented method of claim 12, further comprising training the machine-learning filters against both positive groups that are well segmented and negative groups that are poorly segmented.

14. The computer-implemented method of claim 9, wherein automatically processing the segmented digital model of the patient's dentition if the segmentation of the segmented digital model of the patient's dentition is ranked meets the threshold rank comprises automatically processing the segmented digital model if the rank of the segmented digital model is greater than the threshold rank.

15. A computer-implemented method comprising:
   identifying one or more outlying regions of the segmented digital model of the patient's dentition having tooth-like color that are outside of any region of the segmented digital model of the patient's dentition that is indicated as teeth;
   estimating a probability that any of the one or more outlying regions are teeth;

scoring the segmentation of the segmented digital model of the patient's dentition based, at least in part, on the probability that any of the one or more outlying regions are teeth;

reprocessing the segmented digital model of the patient's dentition if the score of the segmented digital model of the patient's dentition is outside of a passing range; and outputting a grade or score of the segmented digital model of the patient's dentition.

16. The computer-implemented method of claim 15, further comprising determining a color quality of a segmented digital model of a patient's dentition.

17. The method of claim 16, further comprising stopping the method if the color quality is below a color quality metric.

18. The method of claim 15, further comprising adjusting the score of the segmentation of the segmented digital model of the patient's dentition based on a comparison between the color values of the segmentation boundary and the color value on either sides of the segmentation boundary.

19. The method of claim 15, wherein identifying one or more outlying regions of the segmented digital model of the patient's dentition having tooth-like color comprises identifying the one or more outlying region having tooth-like blue and green color values.

20. The method of claim 15, wherein estimating the probability comprises basing the probability on at least one or more of: the size of the outlying region, the relative boundary size of the outlying region, the presence or absence of a cusp on the outlying region, the presence of sharp edges on the outlying region and the shape of the outlying region.

* * * * *